United States Patent
Li et al.

(10) Patent No.: US 6,514,690 B1
(45) Date of Patent: Feb. 4, 2003

(54) IMMUNOREACTIVE ANTIGENS OF HEPATITIS E VIRUS

(75) Inventors: Fan Li, Beijing (CN); Zhuang Hui, Beijing (CN); David Andrew Anderson, Brunswick (AU); Stephen Alistair Logarnini, East St. Kilda (AU); Joseph Torresi, Eltham (AU)

(73) Assignee: The Macfarlane Burnet Centre for Medical Research Limited, Victoria (AU)

(*) Notice: Subject to any disclaimer, the term of this patent is extended or adjusted under 35 U.S.C. 154(b) by 0 days.

(21) Appl. No.: 09/172,699

(22) Filed: Oct. 14, 1998

Related U.S. Application Data

(63) Continuation-in-part of application No. 08/617,927, filed as application No. PCT/AU94/00572 on Sep. 23, 1994, now abandoned.

(30) Foreign Application Priority Data

Sep. 23, 1993 (AU) .............................. PM 1423
Dec. 15, 1993 (AU) .............................. PM 2964

(51) Int. Cl.⁷ ........................... C12Q 1/70; G01N 33/53
(52) U.S. Cl. ........................... 435/5; 435/7.1; 435/975; 530/324; 530/350
(58) Field of Search .................... 435/5, 7.1, 975, 435/235.1; 530/324, 350; 424/189.1, 228.1

(56) References Cited

U.S. PATENT DOCUMENTS 5,741,490 A * 4/1998 Reyes et al. ............. 424/189.1
5,770,689 A * 6/1998 Reyes et al. ................. 530/324

FOREIGN PATENT DOCUMENTS

WO 95/08632 * 3/1995 ........... C12N/15/51

OTHER PUBLICATIONS

Kaur et al. Proceedings of the National Academy of Sciences USA 89:3885–3858, May, 1992.*

He et al. Journal of Clinical Microbiology 31(8): 2167–2173, Aug. 1993.*

Purdy et al. Archives of Virology 123:335–349, 1992.*

Favorov et al. Journal of Medical Virology 36:246–250, 1992.*

Talwar et al. Diagnostics for the tropical countries. Journal of immunological methods 150:121–132, 1992.*

Hengen, P. Kit wars. TIBS 19:46–47, Jan. 1994.*

* cited by examiner

Primary Examiner—Mary E. Mosher
(74) Attorney, Agent, or Firm—Scully, Scott, Murphy & Presser

(57) ABSTRACT

The present invention relates generally to molecules such as peptides, polypeptides and proteins which carry epitopes and in particular B cell epitopes from antigenic proteins encoded by Hepatitis E Virus. These molecules are selectively immunoreactive to convalescent and/or acute phase circulating antibodies to the Hepatitis E Virus and are useful in the development of diagnostic therapeutical and prophylactic agents for Hepatitis E Virus.

18 Claims, 23 Drawing Sheets

Figure 1a

```
ATG CGC CCT CGG CCT ATT TTG CTG TTG CTC ATG TTT CTG CCT ATG        48
Met Arg Pro Arg Pro Ile Leu Leu Leu Leu Met Phe Leu Pro Met
  1               5                  10                 15

CTG CCC GCG CCA CCG CCC GGT CAG CCG CCC GGT TCT GGC CGC CGT        96
Leu Pro Ala Pro Pro Pro Gly Gln Pro Pro Gly Ser Gly Arg Arg
             20                  25                  30

CGC AGC GGC GGT TCC GGT GGT GGT TTC TGG GGT GAC CGG GTT GAT TCT   144
Arg Ser Gly Gly Ser Gly Gly Gly Phe Trp Gly Asp Arg Val Asp Ser
         35                  40                  45

CAG CCC TTC GCA ATC CCC TAT ATT CAT CCA ACC AAC CCC TTC GCC CCC   192
Gln Pro Phe Ala Ile Pro Tyr Ile His Pro Thr Asn Pro Phe Ala Pro
     50                  55                  60

GAT GTC ACC GCT GCG GCC GGG GCT GGA CCT CGT GTT CGC CAA CCC GCC   240
Asp Val Thr Ala Ala Ala Gly Ala Gly Pro Arg Val Arg Gln Pro Ala
 65                  70                  75                  80

CGA CCA CTC GGC TCC GCT TGG CGT GAC CAG GCC CAG CGC CCC GCC GTT   288
Arg Pro Leu Gly Ser Ala Trp Arg Asp Gln Ala Gln Arg Pro Ala Val
             85                  90                  95

GCC TCA CGT CGT AGA CCT ACC ACA GCT GGG GCC GCC CCG CTA ACC GCG   336
Ala Ser Arg Arg Arg Pro Thr Thr Ala Gly Ala Ala Pro Leu Thr Ala
            100                 105                 110
```

Figure 1b

```
GTC GCT CCG GCC CAT GAC ACC CCG CCA GTG CCT GAT GTT GAC TCC CGC      384
Val Ala Pro Ala His Asp Thr Pro Pro Val Pro Asp Val Asp Ser Arg
            115                 120                 125

GGC GCC ATC CTG CGC CGG CAG TAT AAC CTA TCA ACA TCT CCC CTT ACT      432
Gly Ala Ile Leu Arg Arg Gln Tyr Asn Leu Ser Thr Ser Pro Leu Thr
            130                 135                 140

TCT TCC GTG GCC ACC GGT ACA AAC TTG CTA GTT CTA TAC GCC GCT CCT CTT  480
Ser Ser Val Ala Thr Gly Thr Asn Leu Val Leu Tyr Ala Ala Pro Leu
            145                 150                 155             160

AGC CCA CTT CTA CCC CTC CAG GAC GGC ACC AAT ACT CAT ATA ATG GCC      528
Ser Pro Leu Leu Pro Leu Gln Asp Gly Thr Asn Thr His Ile Met Ala
            165                 170                 175

ACA GAA GCT TCT AAT TAT GCC CAG TAC CGG GTT GCT CGT GCC ACA ATT      576
Thr Glu Ala Ser Asn Tyr Ala Gln Tyr Arg Val Ala Arg Ala Thr Ile
            180                 185                 190

CGC TAC CGC CCG CTG GTC CCC AAC GCT GTT GGT TAC GGC ATC TCC          624
Arg Tyr Arg Pro Leu Val Pro Asn Ala Val Gly Tyr Ala Ile Ser
            195                 200                 205

ATC TCG TTC TGG CCA CAG ACC ACC ACC CCG ACG TCC GTT GAC ATG          672
Ile Ser Phe Trp Pro Gln Thr Thr Thr Pro Thr Ser Val Asp Met
            210                 215                 220

AAT TCA ATA ACC TCG ACG GAT GTT CGT ATT TTA GTC CAG CCC GGC ATA      720
Asn Ser Ile Thr Ser Thr Asp Val Arg Ile Leu Val Gln Pro Gly Ile
            225                 230                 235             240
```

Figure 1c

```
GCC TCC GAG CTT GTT ATC CCA AGT GAG CGC CTA CAC TAC CGT AAC CAA      768
Ala Ser Glu Leu Val Ile Pro Ser Glu Arg Leu His Tyr Arg Asn Gln
                245                 250                 255

GGT TGG CGC TCT GTT GAG ACC TCC GGG GTG GCG GAG GAG GAG GCC ACC      816
Gly Trp Arg Ser Val Glu Thr Ser Gly Val Ala Glu Glu Glu Ala Thr
            260                 265                 270

TCT GGT CTT GTT ATG CTC TGC ATA CAT GGC TCA CCT GTA AAT TCT TAT      864
Ser Gly Leu Val Met Leu Cys Ile His Gly Ser Pro Val Asn Ser Tyr
        275                 280                 285

ACT AAT ACA CCT TAT ACC GGT GCC CTC GGG CTG TTG GAC TTT GCC CTC      912
Thr Asn Thr Pro Tyr Thr Gly Ala Leu Gly Leu Leu Asp Phe Ala Leu
    290                 295                 300

GAA CTT GAG TTC CGC AAC CTC ACC CCC GGT AAT ACC AAC ACG CGG GTC      960
Glu Leu Glu Phe Arg Asn Leu Thr Pro Gly Asn Thr Asn Thr Arg Val
305                 310                 315                 320

TCC CGT TAC TCC AGC ACT GCC ACT GCC CGT CAC CGC CTT CGT CGC GGT GCA GAT     1008
Ser Arg Tyr Ser Ser Thr Ala Thr Ala Arg His Arg Leu Arg Arg Gly Ala Asp
                325                 330                 335

GGG ACT GCC GAG CTT ACC ACC ACG GCT GCT ACC CGC TTC ATG AAG GAC     1056
Gly Thr Ala Glu Leu Thr Thr Thr Ala Ala Thr Arg Phe Met Lys Asp
            340                 345                 350

CTC TAT TTT ACT AGT ACT AAT GGT GTC GGT GAG ATC GGC CGT GGG ATA     1104
Leu Tyr Phe Thr Ser Thr Asn Gly Val Gly Glu Ile Gly Arg Gly Ile
        355                 360                 365
```

Figure 1d

```
GCG CTT ACC CTG TTT AAC CTT GCT GAC ACC CTG CTT GGC GGT CTA CCG         1152
Ala Leu Thr Leu Phe Asn Leu Ala Asp Thr Leu Leu Gly Gly Leu Pro
370                 375                 380

ACA GAA TTG ATT TCG TCG GCT GGT GGC CAG CTG TTC TAC TCT CGT CCC         1200
Thr Glu Leu Ile Ser Ser Ala Gly Gly Gln Leu Phe Tyr Ser Arg Pro
385                 390                 395                 400

GTC GTC TCA GCC AAT GGC GAG CCG ACT GTT AAG CTT TAT ACA TCT GTA         1248
Val Val Ser Ala Asn Gly Glu Pro Thr Val Lys Leu Tyr Thr Ser Val
        405                 410                 415

GAG AAT GCT CAG CAG GAT AAG GGT ATT GCA ATC CCG CAT GAC ATC GAC         1296
Glu Asn Ala Gln Gln Asp Lys Gly Ile Ala Ile Pro His Asp Ile Asp
420                 425                 430

CTC GGG GAG CGA TCT CGT GTA GTT ATT CAG GAT TAT GAC AAC CAA CAT GAG     1344
Leu Gly Glu Arg Ser Arg Val Val Ile Gln Asp Tyr Asp Asn Gln His Glu
435                 440                 445

CAG GAC CGA CCG ACA CCT TCC CCA GCC CCA TCG CGC CCT TTT TCT GTC         1392
Gln Asp Arg Pro Thr Pro Ser Pro Ala Pro Ser Arg Pro Phe Ser Val
450                 455                 460

CTC CGA GCT AAT GAT GTG CTT TGG CTT TCT CTC ACC GCT GCC GAG TAT         1440
Leu Arg Ala Asn Asp Val Leu Trp Leu Ser Leu Thr Ala Ala Glu Tyr
465                 470                 475                 480

GAC CAG TCC ACT TAC GGC TCT TCG ACC GGC CCA GTC TAT GTC TCT GAC         1488
Asp Gln Ser Thr Tyr Gly Ser Ser Thr Gly Pro Val Tyr Val Ser Asp
            485                 490                 495
```

Figure 1e

```
TCT GTG ACC TTG GTT AAT GTT GCG ACC GGC GCG CAG GCC GTT GCC CGG    1536
Ser Val Thr Leu Val Asn Val Ala Thr Gly Ala Gln Ala Val Ala Arg
            500                 505                 510

TCA CTC GAC TGG ACC AAG GTC ACA CTT GAT GGT CGC CCC CTT TCC ACC    1584
Ser Leu Asp Trp Thr Lys Val Thr Leu Asp Gly Arg Pro Leu Ser Thr
            515                 520                 525

ATC CAG CAG TAT TCA AAG ACC TTC TTT GTC CTG CCG CTC CGC GGT AAG    1632
Ile Gln Gln Tyr Ser Lys Thr Phe Phe Val Leu Pro Leu Arg Gly Lys
            530                 535                 540

CTC TCC TTT TGG GAG GCA GGT ACT ACT AAA GCC GGG TAC CCT TAT AAT    1680
Leu Ser Phe Trp Glu Ala Gly Thr Thr Lys Ala Gly Tyr Pro Tyr Asn
            545                 550                 555                 560

TAT AAC ACC ACT GCT AGT GAC CAA CTG CTC GTT GAG AAT GCC GCT GGG    1728
Tyr Asn Thr Thr Ala Ser Asp Gln Leu Leu Val Glu Asn Ala Ala Gly
            565                 570                 575

CAT CGG GTT GCT ATT TCC ACT TAC ACC AGC CTG GGT GCT GGT CCC       1776
His Arg Val Ala Ile Ser Thr Tyr Thr Ser Leu Gly Ala Gly Pro
            580                 585                 590

GTC TCT ATT TCC GCG GTT GCT GTT TTA GCC CCC CAC TCC CTA GCA       1824
Val Ser Ile Ser Ala Val Ala Val Leu Ala Pro His Ser Leu Ala
            595                 600                 605

TTG CTT GAG GAT ACC ATG GAC TAC CCT GCC CGC GCC CAT ACT TTC GAT    1872
Leu Leu Glu Asp Thr Met Asp Tyr Pro Ala Arg Ala His Thr Phe Asp
            610                 615                 620
```

Figure 1f

```
GAC TTC TGC CCG GAG TGC CGC CCC CTT GGC CTC CAG GGC TGT GCT TTT    1920
Asp Phe Cys Pro Glu Cys Arg Pro Leu Gly Leu Gln Gly Cys Ala Phe
625                 630                 635                 640

CAG TCT ACT GTC GCT GAG CTT CAG CGC CTT AAG ATG AAG GTG GGT AAA    1968
Gln Ser Thr Val Ala Glu Leu Gln Arg Leu Lys Met Lys Val Gly Lys
        645                 650                 655

ACT CGG GAG TTA TAGT    1990
Thr Arg Glu Leu
            660
```

```
ATG AAT AAC ATG TCT TTT GCT GCG CCC ATG GGT TCG CGA CCA TGC GCC    48
Met Asn Asn Met Ser Phe Ala Ala Pro Met Gly Ser Arg Pro Cys Ala
 1               5                  10                  15

CTC GGC CTA TTT TGC TGT TGC TCC TCA TGT TTC TGC CTA TGC TGC CCG    96
Leu Gly Leu Phe Cys Cys Cys Ser Ser Cys Phe Cys Leu Cys Cys Pro
                20                  25                  30

CGC CAC CGC CCG GTC AGC CGT CTG GCC GCC GTC GTG GGC GGC GCA GCG   144
Arg His Arg Pro Val Ser Arg Leu Ala Ala Val Val Gly Gly Ala Ala
                35                  40                  45

GCG GTT CCG GCG GTG GTT TCT GGG GTG ACC GGG TTG ATT CTC AGC CCT   192
Ala Val Pro Ala Val Val Ser Gly Val Thr Gly Leu Ile Leu Ser Pro
 50                  55                  60

TCG CAA TCC CCT ATA TTC ATC CAA CCA ACC CCT TCG CCC CCG ATG TCA   240
Ser Gln Ser Pro Ile Phe Ile Gln Pro Thr Pro Ser Pro Pro Met Ser
 65                  70                  75                  80
```

Figure 2b

```
CCG CTG CGG CCG GGG CTG GAC CTC GTG TTC GCC AAC CCG CCC GAC CAC    288
Pro Leu Arg Pro Gly Leu Asp Leu Val Phe Ala Asn Pro Pro Asp His
                85                          90                 95

TCG GCT CCG CTT GGC GTG ACC AGG CCC AGC GCC CCG TTG CCT CAC        336
Ser Ala Pro Leu Gly Val Thr Arg Pro Ser Ala Pro Leu Pro His
            100                         105                110

GTC GTA GAC CTA CCA CAG CTG GGG CCG CGC CGC TAA                    372
Val Val Asp Leu Pro Gln Leu Gly Pro Arg Arg
            115                         120
```

Detection of Anti-HEV IgG for Aboriginal Sera
by Genelabs ELISA Kit and Western Blot

|  |  | Western Blot | | Total |
|---|---|---|---|---|
|  |  | + | − |  |
| Genelabs Kit | + | 5 | 1 | 6 |
|  |  | 6 | 148 | 154 |
|  | Total | 11 | 149 | 160 |

Figure 4

Patient serum, 7 months after
onset, Mexico strain

Figure 10

SEQUENCE LISTING

<160> NUMBER OF SEQ ID NOS: 24

<210> SEQ ID NO 1
<211> LENGTH: 1984
<212> TYPE: DNA
<213> ORGANISM: Homo sapiens
<220> FEATURE:
<221> NAME/KEY: CDS
<222> LOCATION: (1)..(1980)

<400> SEQUENCE: 1

```
atg cgc cct cgg cct att ttg ctg ttg ctc ctc atg ttt ctg cct atg        48
Met Arg Pro Arg Pro Ile Leu Leu Leu Leu Leu Met Phe Leu Pro Met
 1               5                  10                  15 ctg ccc gcg cca ccg ccc ggt cag ccg tct ggc cgc cgt cgt ggg cgg        96
Leu Pro Ala Pro Pro Pro Gly Gln Pro Ser Gly Arg Arg Arg Gly Arg
             20                  25                  30 cgc agc ggc ggt tcc ggc ggt ggt ttc tgg ggt gac cgg gtt gat tct       144
Arg Ser Gly Gly Ser Gly Gly Gly Phe Trp Gly Asp Arg Val Asp Ser
         35                  40                  45 cag ccc ttc gca atc ccc tat att cat cca acc aac ccc ttc gcc ccc       192
Gln Pro Phe Ala Ile Pro Tyr Ile His Pro Thr Asn Pro Phe Ala Pro
     50                  55                  60 gat gtc acc gct gcg gcc ggg gct gga cct cgt gtt cgc caa ccc gcc       240
Asp Val Thr Ala Ala Ala Gly Ala Gly Pro Arg Val Arg Gln Pro Ala
 65                  70                  75                  80 cga cca ctc ggc tcc gct tgg cgt gac cag gcc cag cgc ccc gcc gtt       288
Arg Pro Leu Gly Ser Ala Trp Arg Asp Gln Ala Gln Arg Pro Ala Val
                 85                  90                  95 gcc tca cgt cgt aga cct acc aca gct ggg gcc gcg ccg cta acc gcg       336
Ala Ser Arg Arg Arg Pro Thr Thr Ala Gly Ala Ala Pro Leu Thr Ala
            100                 105                 110 gtc gct ccg gcc cat gac acc ccg cca gtg cct gat gtt gac tcc cgc       384
Val Ala Pro Ala His Asp Thr Pro Pro Val Pro Asp Val Asp Ser Arg
        115                 120                 125 ggc gcc atc ctg cgc cgg cag tat aac cta tca aca tct ccc ctt act       432
Gly Ala Ile Leu Arg Arg Gln Tyr Asn Leu Ser Thr Ser Pro Leu Thr
    130                 135                 140 tct tcc gtg gcc acc ggt aca aac ttg gtt cta tac gcc gct cct ctt       480
Ser Ser Val Ala Thr Gly Thr Asn Leu Val Leu Tyr Ala Ala Pro Leu
145                 150                 155                 160 agc cca ctt cta ccc ctc cag gac ggc acc aat act cat ata atg gcc       528
Ser Pro Leu Leu Pro Leu Gln Asp Gly Thr Asn Thr His Ile Met Ala
                165                 170                 175 aca gaa gct tct aat tat gcc cag tac cgg gtt gct cgt gcc aca att       576
Thr Glu Ala Ser Asn Tyr Ala Gln Tyr Arg Val Ala Arg Ala Thr Ile
            180                 185                 190 cgc tac cgc ccg ctg gtc ccc aac gct gtt ggt ggc tac gcc atc tcc       624
Arg Tyr Arg Pro Leu Val Pro Asn Ala Val Gly Gly Tyr Ala Ile Ser
        195                 200                 205
```

```
atc tcg ttc tgg cca cag acc acc acc acc ccg acg tcc gtt gac atg        672
Ile Ser Phe Trp Pro Gln Thr Thr Thr Thr Pro Thr Ser Val Asp Met
210                 215                 220 aat tca ata acc tcg acg gat gtt cgt att tta gtc cag ccc ggc ata        720
Asn Ser Ile Thr Ser Thr Asp Val Arg Ile Leu Val Gln Pro Gly Ile
225                 230                 235                 240 gcc tcc gag ctt gtt atc cca agt gag cgc cta cac tac cgt aac caa        768
Ala Ser Glu Leu Val Ile Pro Ser Glu Arg Leu His Tyr Arg Asn Gln
            245                 250                 255 ggt tgg cgc tct gtt gag acc tcc ggg gtg gcg gag gag gag gcc acc        816
Gly Trp Arg Ser Val Glu Thr Ser Gly Val Ala Glu Glu Glu Ala Thr
        260                 265                 270 tct ggt ctt gtt atg ctc tgc ata cat ggc tca cct gta aat tct tat        864
Ser Gly Leu Val Met Leu Cys Ile His Gly Ser Pro Val Asn Ser Tyr
    275                 280                 285 act aat aca cct tat acc ggt gcc ctc ggg ctg ttg gac ttt gcc ctc        912
Thr Asn Thr Pro Tyr Thr Gly Ala Leu Gly Leu Leu Asp Phe Ala Leu
290                 295                 300 gaa ctt gag ttc cgc aac ctc acc ccc ggt aat acc aac acg cgg gtc        960
Glu Leu Glu Phe Arg Asn Leu Thr Pro Gly Asn Thr Asn Thr Arg Val
305                 310                 315                 320 tcc cgt tac tcc agc act gcc cgt cac cgc ctt cgt cgc ggt gca gat       1008
Ser Arg Tyr Ser Ser Thr Ala Arg His Arg Leu Arg Arg Gly Ala Asp
            325                 330                 335 ggg act gcc gag ctt acc acc acg gct gct acc cgc ttc atg aag gac       1056
Gly Thr Ala Glu Leu Thr Thr Thr Ala Ala Thr Arg Phe Met Lys Asp
        340                 345                 350 ctc tat ttt act agt act aat ggt gtc ggt gag atc ggc cgt ggg ata       1104
Leu Tyr Phe Thr Ser Thr Asn Gly Val Gly Glu Ile Gly Arg Gly Ile
    355                 360                 365 gcg ctt acc ctg ttt aac ctt gct gac acc ctg ctt ggc ggt cta ccg       1152
Ala Leu Thr Leu Phe Asn Leu Ala Asp Thr Leu Leu Gly Gly Leu Pro
370                 375                 380 aca gaa ttg att tcg tcg gct ggt ggc cag ctg ttc tac tct cgt ccc       1200
Thr Glu Leu Ile Ser Ser Ala Gly Gly Gln Leu Phe Tyr Ser Arg Pro
385                 390                 395                 400 gtc gtc tca gcc aat ggc gag ccg act gtt aag ctt tat aca tct gta       1248
Val Val Ser Ala Asn Gly Glu Pro Thr Val Lys Leu Tyr Thr Ser Val
            405                 410                 415 gag aat gct cag cag gat aag ggt att gca atc ccg cat gac atc gac       1296
Glu Asn Ala Gln Gln Asp Lys Gly Ile Ala Ile Pro His Asp Ile Asp
        420                 425                 430 ctc ggg gag tct cgt gta gtt att cag gat tat gac aac caa cat gag       1344
Leu Gly Glu Ser Arg Val Val Ile Gln Asp Tyr Asp Asn Gln His Glu
    435                 440                 445 cag gac cga ccg aca cct tcc cca gcc cca tcg cgc cct ttt tct gtc       1392
Gln Asp Arg Pro Thr Pro Ser Pro Ala Pro Ser Arg Pro Phe Ser Val
450                 455                 460 ctc cga gct aat gat gtg ctt tgg ctt tct ctc acc gct gcc gag tat       1440
Leu Arg Ala Asn Asp Val Leu Trp Leu Ser Leu Thr Ala Ala Glu Tyr
465                 470                 475                 480 gac cag tcc act tac ggc tct tcg acc ggc cca gtc tat gtc tct gac       1488
Asp Gln Ser Thr Tyr Gly Ser Ser Thr Gly Pro Val Tyr Val Ser Asp
            485                 490                 495 tct gtg acc ttg gtt aat gtt gcg acc ggc gcg cag gcc gtt gcc cgg       1536
Ser Val Thr Leu Val Asn Val Ala Thr Gly Ala Gln Ala Val Ala Arg
        500                 505                 510 tca ctc gac tgg acc aag gtc aca ctt gat ggt cgc ccc ctt tcc acc       1584
Ser Leu Asp Trp Thr Lys Val Thr Leu Asp Gly Arg Pro Leu Ser Thr
    515                 520                 525
```

-continued

```
atc cag cag tat tca aag acc ttc ttt gtc ctg ccg ctc cgc ggt aag     1632
Ile Gln Gln Tyr Ser Lys Thr Phe Phe Val Leu Pro Leu Arg Gly Lys
    530                 535                 540 ctc tcc ttt tgg gag gca ggt act act aaa gcc ggg tac cct tat aat     1680
Leu Ser Phe Trp Glu Ala Gly Thr Thr Lys Ala Gly Tyr Pro Tyr Asn
545                 550                 555                 560 tat aac acc act gct agt gac caa ctg ctc gtt gag aat gcc gct ggg     1728
Tyr Asn Thr Thr Ala Ser Asp Gln Leu Leu Val Glu Asn Ala Ala Gly
                565                 570                 575 cat cgg gtt gct att tcc act tac acc act agc ctg ggt gct ggt ccc     1776
His Arg Val Ala Ile Ser Thr Tyr Thr Thr Ser Leu Gly Ala Gly Pro
        580                 585                 590 gtc tct att tcc gcg gtt gct gtt tta gcc ccc cac tcc gcg cta gca     1824
Val Ser Ile Ser Ala Val Ala Val Leu Ala Pro His Ser Ala Leu Ala
            595                 600                 605 ttg ctt gag gat acc atg gac tac cct gcc cgc gcc cat act ttc gat     1872
Leu Leu Glu Asp Thr Met Asp Tyr Pro Ala Arg Ala His Thr Phe Asp
610                 615                 620 gac ttc tgc ccg gag tgc cgc ccc ctt ggc ctc cag ggc tgt gct ttt     1920
Asp Phe Cys Pro Glu Cys Arg Pro Leu Gly Leu Gln Gly Cys Ala Phe
625                 630                 635                 640 cag tct act gtc gct gag ctt cag cgc ctt aag atg aag gtg ggt aaa     1968
Gln Ser Thr Val Ala Glu Leu Gln Arg Leu Lys Met Lys Val Gly Lys
                645                 650                 655 act cgg gag tta tagt                                                1984
Thr Arg Glu Leu
        660
```

<210> SEQ ID NO 2
<211> LENGTH: 660
<212> TYPE: PRT
<213> ORGANISM: Homo sapiens

<400> SEQUENCE: 2

```
Met Arg Pro Arg Pro Ile Leu Leu Leu Leu Met Phe Leu Pro Met
  1               5                  10                  15

Leu Pro Ala Pro Pro Gly Gln Pro Ser Gly Arg Arg Gly Arg
            20                  25                  30

Arg Ser Gly Gly Ser Gly Gly Gly Phe Trp Gly Asp Arg Val Asp Ser
        35                  40                  45

Gln Pro Phe Ala Ile Pro Tyr Ile His Pro Thr Asn Pro Phe Ala Pro
    50                  55                  60

Asp Val Thr Ala Ala Gly Ala Gly Pro Arg Val Arg Gln Pro Ala
65                  70                  75                  80

Arg Pro Leu Gly Ser Ala Trp Arg Asp Gln Ala Gln Arg Pro Ala Val
                85                  90                  95

Ala Ser Arg Arg Arg Pro Thr Thr Ala Gly Ala Ala Pro Leu Thr Ala
            100                 105                 110

Val Ala Pro Ala His Asp Thr Pro Val Pro Asp Val Asp Ser Arg
        115                 120                 125

Gly Ala Ile Leu Arg Arg Gln Tyr Asn Leu Ser Thr Ser Pro Leu Thr
    130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
            180                 185                 190
```

-continued

```
Arg Tyr Arg Pro Leu Val Pro Asn Ala Val Gly Gly Tyr Ala Ile Ser
        195                 200                 205

Ile Ser Phe Trp Pro Gln Thr Thr Thr Pro Thr Ser Val Asp Met
    210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Pro Val Asn Ser Tyr
            275                 280                 285

Thr Asn Thr Pro Tyr Thr Gly Ala Leu Gly Leu Leu Asp Phe Ala Leu
    290                 295                 300

Glu Leu Glu Phe Arg Asn Leu Thr Pro Gly Asn Thr Asn Thr Arg Val
305                 310                 315                 320

Ser Arg Tyr Ser Ser Thr Ala Arg His Arg Leu Arg Arg Gly Ala Asp
                325                 330                 335

Gly Thr Ala Glu Leu Thr Thr Ala Ala Thr Arg Phe Met Lys Asp
            340                 345                 350

Leu Tyr Phe Thr Ser Thr Asn Gly Val Gly Glu Ile Gly Arg Gly Ile
    355                 360                 365

Ala Leu Thr Leu Phe Asn Leu Ala Asp Thr Leu Leu Gly Gly Leu Pro
    370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Ala Ile Pro His Asp Ile Asp
            420                 425                 430

Leu Gly Glu Ser Arg Val Val Ile Gln Asp Tyr Asp Asn Gln His Glu
            435                 440                 445

Gln Asp Arg Pro Thr Pro Ser Pro Ala Pro Ser Arg Pro Phe Ser Val
    450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Gly Pro Val Tyr Val Ser Asp
                485                 490                 495

Ser Val Thr Leu Val Asn Val Ala Thr Gly Ala Gln Ala Val Ala Arg
            500                 505                 510

Ser Leu Asp Trp Thr Lys Val Thr Leu Asp Gly Arg Pro Leu Ser Thr
            515                 520                 525

Ile Gln Gln Tyr Ser Lys Thr Phe Phe Val Leu Pro Leu Arg Gly Lys
    530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Leu Leu Val Glu Asn Ala Ala Gly
                565                 570                 575

His Arg Val Ala Ile Ser Thr Tyr Thr Thr Ser Leu Gly Ala Gly Pro
            580                 585                 590

Val Ser Ile Ser Ala Val Ala Val Leu Ala Pro His Ser Ala Leu Ala
    595                 600                 605
```

-continued

```
Leu Leu Glu Asp Thr Met Asp Tyr Pro Ala Arg Ala His Thr Phe Asp
    610                 615                 620
Asp Phe Cys Pro Glu Cys Arg Pro Leu Gly Leu Gln Gly Cys Ala Phe
625                 630                 635                 640
Gln Ser Thr Val Ala Glu Leu Gln Arg Leu Lys Met Lys Val Gly Lys
                645                 650                 655
Thr Arg Glu Leu
            660

<210> SEQ ID NO 3
<211> LENGTH: 372
<212> TYPE: DNA
<213> ORGANISM: Homo sapiens
<220> FEATURE:
<221> NAME/KEY: CDS
<222> LOCATION: (1)..(369)

<400> SEQUENCE: 3 atg aat aac atg tct ttt gct gcg ccc atg ggt tcg cga cca tgc gcc      48
Met Asn Asn Met Ser Phe Ala Ala Pro Met Gly Ser Arg Pro Cys Ala
 1               5                  10                  15 ctc ggc cta ttt tgc tgt tgc tcc tca tgt ttc tgc cta tgc tgc ccg      96
Leu Gly Leu Phe Cys Cys Cys Ser Ser Cys Phe Cys Leu Cys Cys Pro
             20                  25                  30 cgc cac cgc ccg gtc agc cgt ctg gcc gcc gtc gtg ggc ggc gca gcg     144
Arg His Arg Pro Val Ser Arg Leu Ala Ala Val Val Gly Gly Ala Ala
         35                  40                  45 gcg gtt ccg gcg gtg gtt tct ggg gtg acc ggg ttg att ctc agc cct     192
Ala Val Pro Ala Val Val Ser Gly Val Thr Gly Leu Ile Leu Ser Pro
     50                  55                  60 tcg caa tcc cct ata ttc atc caa cca acc cct tcg ccc ccg atg tca     240
Ser Gln Ser Pro Ile Phe Ile Gln Pro Thr Pro Ser Pro Pro Met Ser
 65                  70                  75                  80 ccg ctg cgg ccg ggg ctg gac ctc gtg ttc gcc aac ccg ccc gac cac     288
Pro Leu Arg Pro Gly Leu Asp Leu Val Phe Ala Asn Pro Pro Asp His
                 85                  90                  95 tcg gct ccg ctt ggc gtg acc agg ccc agc gcc ccg ccg ttg cct cac     336
Ser Ala Pro Leu Gly Val Thr Arg Pro Ser Ala Pro Pro Leu Pro His
            100                 105                 110 gtc gta gac cta cca cag ctg ggg ccg cgc cgc taa                     372
Val Val Asp Leu Pro Gln Leu Gly Pro Arg Arg
        115                 120

<210> SEQ ID NO 4
<211> LENGTH: 123
<212> TYPE: PRT
<213> ORGANISM: Homo sapiens

<400> SEQUENCE: 4

Met Asn Asn Met Ser Phe Ala Ala Pro Met Gly Ser Arg Pro Cys Ala
 1               5                  10                  15

Leu Gly Leu Phe Cys Cys Cys Ser Ser Cys Phe Cys Leu Cys Cys Pro
             20                  25                  30

Arg His Arg Pro Val Ser Arg Leu Ala Ala Val Val Gly Gly Ala Ala
         35                  40                  45

Ala Val Pro Ala Val Val Ser Gly Val Thr Gly Leu Ile Leu Ser Pro
     50                  55                  60

Ser Gln Ser Pro Ile Phe Ile Gln Pro Thr Pro Ser Pro Pro Met Ser
 65                  70                  75                  80
```

```
Pro Leu Arg Pro Gly Leu Asp Leu Val Phe Ala Asn Pro Pro Asp His
            85                  90                  95

Ser Ala Pro Leu Gly Val Thr Arg Pro Ser Ala Pro Pro Leu Pro His
           100                 105                 110

Val Val Asp Leu Pro Gln Leu Gly Pro Arg Arg
           115                 120
```

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: HEV Primer
      (ORF3-forward)

<400> SEQUENCE: 5
gtgaattcat gaataacatg tcttttgc                                    28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: HEV Primer
      (ORF3-reverse)

<400> SEQUENCE: 6
gtgaattctt agcggcgcgg ccccagct                                    28

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: HEV Primer
      (ORF2-forward)

<400> SEQUENCE: 7
gtgaattcca gctgttctac tcccgtcc                                    28

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:HEV Primer
      (ORF2-reverse)

<400> SEQUENCE: 8
gtgaattcgg cactccgttt atttgatgtt                                  30

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:HEV Primer
      (ORF2.0 forward)

<400> SEQUENCE: 9
tcgtagacct accacagctg                                             20

<210> SEQ ID NO 10
<211> LENGTH: 20
<212> TYPE: DNA
<213> ORGANISM: Artificial Sequence

```
<220> FEATURE:
<223> OTHER INFORMATION: Description of Artificial Sequence:HEV Primer
      (ORF 2.0 reverse)

<400> SEQUENCE: 10
tcttaaggcg ctgaagctca                                                    20

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:HEV Primer
      (ORF 2.3 forward)

<400> SEQUENCE: 11
gtggatccat gcgccctcgg cctattttgt                                         30

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:HEV Primer
      (ORF 2.3 reverse)

<400> SEQUENCE: 12
gtgaattctt agcggcgcgg ccccagct                                           28

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:HEV Primer
      (P2)

<400> SEQUENCE: 13
tcgtagacct accacagctg                                                    20

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:HEV Primer
      (P5019)

<400> SEQUENCE: 14
cacaagctca gaggctatgc cg                                                 22

<210> SEQ ID NO 15
<211> LENGTH: 1658
<212> TYPE: DNA
<213> ORGANISM: Homo sapiens
<220> FEATURE:
<221> NAME/KEY: CDS
<222> LOCATION: (2)..(1657)

<400> SEQUENCE: 15 t cgt aga cct acc aca gct ggg gcc gcg ccg cta acc gcg gtc gct ccg       49
  Arg Arg Pro Thr Thr Ala Gly Ala Ala Pro Leu Thr Ala Val Ala Pro
   1               5                  10                  15 gcc cat gac acc ccg cca gtg cct gat gtt gac tcc cgc ggc gcc atc         97
Ala His Asp Thr Pro Pro Val Pro Asp Val Asp Ser Arg Gly Ala Ile
            20                  25                  30
```

```
ctg cgc cgg cag tat aac cta tca aca tct ccc ctt act tct tcc gtg      145
Leu Arg Arg Gln Tyr Asn Leu Ser Thr Ser Pro Leu Thr Ser Ser Val
         35                  40                  45 gcc acc ggt aca aac ttg gtt cta tac gcc gct cct ctt agc cca ctt      193
Ala Thr Gly Thr Asn Leu Val Leu Tyr Ala Ala Pro Leu Ser Pro Leu
 50                  55                  60 cta ccc ctc cag gac ggc acc aat act cat ata atg gcc aca gaa gct      241
Leu Pro Leu Gln Asp Gly Thr Asn Thr His Ile Met Ala Thr Glu Ala
 65                  70                  75                  80 tct aat tat gcc cag tac cgg gtt gct cgt gcc aca att cgc tac cgc      289
Ser Asn Tyr Ala Gln Tyr Arg Val Ala Arg Ala Thr Ile Arg Tyr Arg
                 85                  90                  95 ccg ctg gtc ccc aac gct gtt ggt ggc tac gcc atc tcc atc tcg ttc      337
Pro Leu Val Pro Asn Ala Val Gly Gly Tyr Ala Ile Ser Ile Ser Phe
            100                 105                 110 tgg cca cag acc acc acc acc ccg acg tcc gtt gac atg aat tca ata      385
Trp Pro Gln Thr Thr Thr Thr Pro Thr Ser Val Asp Met Asn Ser Ile
            115                 120                 125 acc tcg acg gat gtt cgt att tta gtc cag ccc ggc ata gcc tcc gag      433
Thr Ser Thr Asp Val Arg Ile Leu Val Gln Pro Gly Ile Ala Ser Glu
130                 135                 140 ctt gtt atc cca agt gag cgc cta cac tac cgt aac caa ggt tgg cgc      481
Leu Val Ile Pro Ser Glu Arg Leu His Tyr Arg Asn Gln Gly Trp Arg
145                 150                 155                 160 tct gtt gag acc tcc ggg gtg gcg gag gag gag gcc acc tct ggt ctt      529
Ser Val Glu Thr Ser Gly Val Ala Glu Glu Glu Ala Thr Ser Gly Leu
                165                 170                 175 gtt atg ctc tgc ata cat ggc tca cct gta aat tct tat act aat aca      577
Val Met Leu Cys Ile His Gly Ser Pro Val Asn Ser Tyr Thr Asn Thr
            180                 185                 190 cct tat acc ggt gcc ctc ggg ctg ttg gac ttt gcc ctc gaa ctt gag      625
Pro Tyr Thr Gly Ala Leu Gly Leu Leu Asp Phe Ala Leu Glu Leu Glu
            195                 200                 205 ttc cgc aac ctc acc ccc ggt aat acc aac acg cgg gtc tcc cgt tac      673
Phe Arg Asn Leu Thr Pro Gly Asn Thr Asn Thr Arg Val Ser Arg Tyr
            210                 215                 220 tcc agc act gcc cgt cac cgc ctt cgt cgc ggt gca gat ggg act gcc      721
Ser Ser Thr Ala Arg His Arg Leu Arg Arg Gly Ala Asp Gly Thr Ala
225                 230                 235                 240 gag ctt acc acc acg gct gct acc cgc ttc atg aag gac ctc tat ttt      769
Glu Leu Thr Thr Thr Ala Ala Thr Arg Phe Met Lys Asp Leu Tyr Phe
                245                 250                 255 act agt act aat ggt gtc ggt gag atc ggc cgt ggg ata gcg ctt acc      817
Thr Ser Thr Asn Gly Val Gly Glu Ile Gly Arg Gly Ile Ala Leu Thr
            260                 265                 270 ctg ttt aac ctt gct gac acc ctg ctt ggc ggt cta ccg aca gaa ttg      865
Leu Phe Asn Leu Ala Asp Thr Leu Leu Gly Gly Leu Pro Thr Glu Leu
            275                 280                 285 att tcg tcg gct ggt ggc cag ctg ttc tac tct cgt ccc gtc gtc tca      913
Ile Ser Ser Ala Gly Gly Gln Leu Phe Tyr Ser Arg Pro Val Val Ser
            290                 295                 300 gcc aat ggc gag ccg act gtt aag ctt tat aca tct gta gag aat gct      961
Ala Asn Gly Glu Pro Thr Val Lys Leu Tyr Thr Ser Val Glu Asn Ala
305                 310                 315                 320 cag cag gat aag ggt att gca atc ccg cat gac atc gac ctc ggg gag     1009
Gln Gln Asp Lys Gly Ile Ala Ile Pro His Asp Ile Asp Leu Gly Glu
                325                 330                 335 tct cgt gta gtt att cag gat tat gac aac caa cat gag cag gac cga     1057
Ser Arg Val Val Ile Gln Asp Tyr Asp Asn Gln His Glu Gln Asp Arg
            340                 345                 350
```

```
ccg aca cct tcc cca gcc cca tcg cgc cct ttt tct gtc ctc cga gct    1105
Pro Thr Pro Ser Pro Ala Pro Ser Arg Pro Phe Ser Val Leu Arg Ala
        355                 360                 365 aat gat gtg ctt tgg ctt tct ctc acc gct gcc gag tat gac cag tcc    1153
Asn Asp Val Leu Trp Leu Ser Leu Thr Ala Ala Glu Tyr Asp Gln Ser
370                 375                 380 act tac ggc tct tcg acc ggc cca gtc tat gtc tct gac tct gtg acc    1201
Thr Tyr Gly Ser Ser Thr Gly Pro Val Tyr Val Ser Asp Ser Val Thr
385                 390                 395                 400 ttg gtt aat gtt gcg acc ggc gcg cag gcc gtt gcc cgg tca ctc gac    1249
Leu Val Asn Val Ala Thr Gly Ala Gln Ala Val Ala Arg Ser Leu Asp
            405                 410                 415 tgg acc aag gtc aca ctt gat ggt cgc ccc ctt tcc acc atc cag cag    1297
Trp Thr Lys Val Thr Leu Asp Gly Arg Pro Leu Ser Thr Ile Gln Gln
            420                 425                 430 tat tca aag acc ttc ttt gtc ctg ccg ctc cgc ggt aag ctc tcc ttt    1345
Tyr Ser Lys Thr Phe Phe Val Leu Pro Leu Arg Gly Lys Leu Ser Phe
            435                 440                 445 tgg gag gca ggt act act aaa gcc ggg tac cct tat aat tat aac acc    1393
Trp Glu Ala Gly Thr Thr Lys Ala Gly Tyr Pro Tyr Asn Tyr Asn Thr
450                 455                 460 act gct agt gac caa ctg ctc gtt gag aat gcc gct ggg cat cgg gtt    1441
Thr Ala Ser Asp Gln Leu Leu Val Glu Asn Ala Ala Gly His Arg Val
465                 470                 475                 480 gct att tcc act tac acc act agc ctg ggt gct ggt ccc gtc tct att    1489
Ala Ile Ser Thr Tyr Thr Thr Ser Leu Gly Ala Gly Pro Val Ser Ile
            485                 490                 495 tcc gcg gtt gct gtt tta gcc ccc cac tcc gcg cta gca ttg ctt gag    1537
Ser Ala Val Ala Val Leu Ala Pro His Ser Ala Leu Ala Leu Leu Glu
            500                 505                 510 gat acc atg gac tac cct gcc cgc gcc cat act ttc gat gac ttc tgc    1585
Asp Thr Met Asp Tyr Pro Ala Arg Ala His Thr Phe Asp Asp Phe Cys
            515                 520                 525 ccg gag tgc cgc ccc ctt ggc ctc cag ggc tgt gct ttt cag tct act    1633
Pro Glu Cys Arg Pro Leu Gly Leu Gln Gly Cys Ala Phe Gln Ser Thr
530                 535                 540 gtc gct gag ctt cag cgc ctt aag a                                  1658
Val Ala Glu Leu Gln Arg Leu Lys
545                 550

<210> SEQ ID NO 16
<211> LENGTH: 552
<212> TYPE: PRT
<213> ORGANISM: Homo sapiens

<400> SEQUENCE: 16

Arg Arg Pro Thr Thr Ala Gly Ala Ala Pro Leu Thr Ala Val Ala Pro
1               5                   10                  15

Ala His Asp Thr Pro Pro Val Pro Asp Val Asp Ser Arg Gly Ala Ile
                20                  25                  30

Leu Arg Arg Gln Tyr Asn Leu Ser Thr Ser Pro Leu Thr Ser Ser Val
            35                  40                  45

Ala Thr Gly Thr Asn Leu Val Leu Tyr Ala Ala Pro Leu Ser Pro Leu
        50                  55                  60

Leu Pro Leu Gln Asp Gly Thr Asn Thr His Ile Met Ala Thr Glu Ala
65                  70                  75                  80

Ser Asn Tyr Ala Gln Tyr Arg Val Ala Arg Ala Thr Ile Arg Tyr Arg
                85                  90                  95
```

```
Pro Leu Val Pro Asn Ala Val Gly Gly Tyr Ala Ile Ser Ile Ser Phe
            100                 105                 110

Trp Pro Gln Thr Thr Thr Pro Thr Ser Val Asp Met Asn Ser Ile
        115                 120                 125

Thr Ser Thr Asp Val Arg Ile Leu Val Gln Pro Gly Ile Ala Ser Glu
130                 135                 140

Leu Val Ile Pro Ser Glu Arg Leu His Tyr Arg Asn Gln Gly Trp Arg
145                 150                 155                 160

Ser Val Glu Thr Ser Gly Val Ala Glu Glu Ala Thr Ser Gly Leu
                165                 170                 175

Val Met Leu Cys Ile His Gly Ser Pro Val Asn Ser Tyr Thr Asn Thr
                180                 185                 190

Pro Tyr Thr Gly Ala Leu Gly Leu Leu Asp Phe Ala Leu Glu Leu Glu
        195                 200                 205

Phe Arg Asn Leu Thr Pro Gly Asn Thr Asn Thr Arg Val Ser Arg Tyr
        210                 215                 220

Ser Ser Thr Ala Arg His Arg Leu Arg Arg Gly Ala Asp Gly Thr Ala
225                 230                 235                 240

Glu Leu Thr Thr Thr Ala Ala Thr Arg Phe Met Lys Asp Leu Tyr Phe
                245                 250                 255

Thr Ser Thr Asn Gly Val Gly Glu Ile Gly Arg Gly Ile Ala Leu Thr
                260                 265                 270

Leu Phe Asn Leu Ala Asp Thr Leu Leu Gly Gly Leu Pro Thr Glu Leu
        275                 280                 285

Ile Ser Ser Ala Gly Gly Gln Leu Phe Tyr Ser Arg Pro Val Val Ser
        290                 295                 300

Ala Asn Gly Glu Pro Thr Val Lys Leu Tyr Thr Ser Val Glu Asn Ala
305                 310                 315                 320

Gln Gln Asp Lys Gly Ile Ala Ile Pro His Asp Ile Asp Leu Gly Glu
                325                 330                 335

Ser Arg Val Val Ile Gln Asp Tyr Asp Asn Gln His Glu Gln Asp Arg
                340                 345                 350

Pro Thr Pro Ser Pro Ala Pro Ser Arg Pro Phe Ser Val Leu Arg Ala
        355                 360                 365

Asn Asp Val Leu Trp Leu Ser Leu Thr Ala Ala Glu Tyr Asp Gln Ser
370                 375                 380

Thr Tyr Gly Ser Ser Thr Gly Pro Val Tyr Val Ser Asp Ser Val Thr
385                 390                 395                 400

Leu Val Asn Val Ala Thr Gly Ala Gln Ala Val Ala Arg Ser Leu Asp
                405                 410                 415

Trp Thr Lys Val Thr Leu Asp Gly Arg Pro Leu Ser Thr Ile Gln Gln
                420                 425                 430

Tyr Ser Lys Thr Phe Phe Val Leu Pro Leu Arg Gly Lys Leu Ser Phe
                435                 440                 445

Trp Glu Ala Gly Thr Thr Lys Ala Gly Tyr Pro Tyr Asn Tyr Asn Thr
        450                 455                 460

Thr Ala Ser Asp Gln Leu Leu Val Glu Asn Ala Ala Gly His Arg Val
465                 470                 475                 480

Ala Ile Ser Thr Tyr Thr Thr Ser Leu Gly Ala Gly Pro Val Ser Ile
                485                 490                 495

Ser Ala Val Ala Val Leu Ala Pro His Ser Ala Leu Ala Leu Leu Glu
                500                 505                 510
```

```
Asp Thr Met Asp Tyr Pro Ala Arg Ala His Thr Phe Asp Asp Phe Cys
        515                 520                 525

Pro Glu Cys Arg Pro Leu Gly Leu Gln Gly Cys Ala Phe Gln Ser Thr
        530                 535                 540

Val Ala Glu Leu Gln Arg Leu Lys
545                 550

<210> SEQ ID NO 17
<211> LENGTH: 803
<212> TYPE: DNA
<213> ORGANISM: Homo sapiens
<220> FEATURE:
<221> NAME/KEY: CDS
<222> LOCATION: (1)..(801)

<400> SEQUENCE: 17 cag ctg ttc tac tct cgt ccc gtc gtc tca gcc aat ggc gag ccg act    48
Gln Leu Phe Tyr Ser Arg Pro Val Val Ser Ala Asn Gly Glu Pro Thr
  1               5                  10                  15 gtt aag ctt tat aca tct gta gag aat gct cag cag gat aag ggt att    96
Val Lys Leu Tyr Thr Ser Val Glu Asn Ala Gln Gln Asp Lys Gly Ile
             20                  25                  30 gca atc ccg cat gac atc gac ctc ggg gag tct cgt gta gtt att cag   144
Ala Ile Pro His Asp Ile Asp Leu Gly Glu Ser Arg Val Val Ile Gln
         35                  40                  45 gat tat gac aac caa cat gag cag gac cga ccg aca cct tcc cca gcc   192
Asp Tyr Asp Asn Gln His Glu Gln Asp Arg Pro Thr Pro Ser Pro Ala
     50                  55                  60 cca tcg cgc cct ttt tct gtc ctc cga gct aat gat gtg ctt tgg ctt   240
Pro Ser Arg Pro Phe Ser Val Leu Arg Ala Asn Asp Val Leu Trp Leu
 65                  70                  75                  80 tct ctc acc gct gcc gag tat gac cag tcc act tac ggc tct tcg acc   288
Ser Leu Thr Ala Ala Glu Tyr Asp Gln Ser Thr Tyr Gly Ser Ser Thr
                 85                  90                  95 ggc cca gtc tat gtc tct gac tct gtg acc ttg gtt aat gtt gcg acc   336
Gly Pro Val Tyr Val Ser Asp Ser Val Thr Leu Val Asn Val Ala Thr
            100                 105                 110 ggc gcg cag gcc gtt gcc cgg tca ctc gac tgg acc aag gtc aca ctt   384
Gly Ala Gln Ala Val Ala Arg Ser Leu Asp Trp Thr Lys Val Thr Leu
        115                 120                 125 gat ggt cgc ccc ctt tcc acc atc cag cag tat tca aag acc ttc ttt   432
Asp Gly Arg Pro Leu Ser Thr Ile Gln Gln Tyr Ser Lys Thr Phe Phe
    130                 135                 140 gtc ctg ccg ctc cgc ggt aag ctc tcc ttt tgg gag gca ggt act act   480
Val Leu Pro Leu Arg Gly Lys Leu Ser Phe Trp Glu Ala Gly Thr Thr
145                 150                 155                 160 aaa gcc ggg tac cct tat aat tat aac acc act gct agt gac caa ctg   528
Lys Ala Gly Tyr Pro Tyr Asn Tyr Asn Thr Thr Ala Ser Asp Gln Leu
                165                 170                 175 ctc gtt gag aat gcc gct ggg cat cgg gtt gct att tcc act tac acc   576
Leu Val Glu Asn Ala Ala Gly His Arg Val Ala Ile Ser Thr Tyr Thr
            180                 185                 190 act agc ctg ggt gct ggt ccc gtc tct att tcc gcg gtt gct gtt tta   624
Thr Ser Leu Gly Ala Gly Pro Val Ser Ile Ser Ala Val Ala Val Leu
        195                 200                 205 gcc ccc cac tcc gcg cta gca ttg ctt gag gat acc atg gac tac cct   672
Ala Pro His Ser Ala Leu Ala Leu Leu Glu Asp Thr Met Asp Tyr Pro
    210                 215                 220 gcc cgc gcc cat act ttc gat gac ttc tgc ccg gag tgc cgc ccc ctt   720
Ala Arg Ala His Thr Phe Asp Asp Phe Cys Pro Glu Cys Arg Pro Leu
225                 230                 235                 240
```

```
ggc ctc cag ggc tgt gct ttt cag tct act gtc gct gag ctt cag cgc    768
Gly Leu Gln Gly Cys Ala Phe Gln Ser Thr Val Ala Glu Leu Gln Arg
                245                 250                 255 ctt aag atg aag gtg ggt aaa act cgg gag tta ta                     803
Leu Lys Met Lys Val Gly Lys Thr Arg Glu Leu
            260                 265
```

<210> SEQ ID NO 18
<211> LENGTH: 267
<212> TYPE: PRT
<213> ORGANISM: Homo sapiens

<400> SEQUENCE: 18

```
Gln Leu Phe Tyr Ser Arg Pro Val Ser Ala Asn Gly Glu Pro Thr
  1               5                  10                  15

Val Lys Leu Tyr Thr Ser Val Glu Asn Ala Gln Gln Asp Lys Gly Ile
                 20                  25                  30

Ala Ile Pro His Asp Ile Asp Leu Gly Glu Ser Arg Val Val Ile Gln
                 35                  40                  45

Asp Tyr Asp Asn Gln His Glu Gln Asp Arg Pro Thr Pro Ser Pro Ala
 50                  55                  60

Pro Ser Arg Pro Phe Ser Val Leu Arg Ala Asn Asp Val Leu Trp Leu
 65                  70                  75                  80

Ser Leu Thr Ala Ala Glu Tyr Asp Gln Ser Thr Tyr Gly Ser Ser Thr
                 85                  90                  95

Gly Pro Val Tyr Val Ser Asp Ser Val Thr Leu Val Asn Val Ala Thr
                100                 105                 110

Gly Ala Gln Ala Val Ala Arg Ser Leu Asp Trp Thr Lys Val Thr Leu
                115                 120                 125

Asp Gly Arg Pro Leu Ser Thr Ile Gln Gln Tyr Ser Lys Thr Phe Phe
                130                 135                 140

Val Leu Pro Leu Arg Gly Lys Leu Ser Phe Trp Glu Ala Gly Thr Thr
145                 150                 155                 160

Lys Ala Gly Tyr Pro Tyr Asn Tyr Asn Thr Thr Ala Ser Asp Gln Leu
                165                 170                 175

Leu Val Glu Asn Ala Ala Gly His Arg Val Ala Ile Ser Thr Tyr Thr
                180                 185                 190

Thr Ser Leu Gly Ala Gly Pro Val Ser Ile Ser Ala Val Ala Val Leu
                195                 200                 205

Ala Pro His Ser Ala Leu Ala Leu Leu Glu Asp Thr Met Asp Tyr Pro
                210                 215                 220

Ala Arg Ala His Thr Phe Asp Asp Phe Cys Pro Glu Cys Arg Pro Leu
225                 230                 235                 240

Gly Leu Gln Gly Cys Ala Phe Gln Ser Thr Val Ala Glu Leu Gln Arg
                245                 250                 255

Leu Lys Met Lys Val Gly Lys Thr Arg Glu Leu
                260                 265
```

<210> SEQ ID NO 19
<211> LENGTH: 1686
<212> TYPE: DNA
<213> ORGANISM: Homo sapiens
<220> FEATURE:
<221> NAME/KEY: CDS
<222> LOCATION: (2)..(1684)

```
<400> SEQUENCE: 19 t cgt aga cct acc aca gct ggg gcc gcg ccg cta acc gcg gtc gct ccg        49
  Arg Arg Pro Thr Thr Ala Gly Ala Ala Pro Leu Thr Ala Val Ala Pro
  1               5                  10                  15 gcc cat gac acc ccg cca gtg cct gat gtt gac tcc cgc ggc gcc atc         97
Ala His Asp Thr Pro Pro Val Pro Asp Val Asp Ser Arg Gly Ala Ile
             20                  25                  30 ctg cgc cgg cag tat aac cta tca aca tct ccc ctt act tct tcc gtg        145
Leu Arg Arg Gln Tyr Asn Leu Ser Thr Ser Pro Leu Thr Ser Ser Val
         35                  40                  45 gcc acc ggt aca aac ttg gtt cta tac gcc gct cct ctt agc cca ctt        193
Ala Thr Gly Thr Asn Leu Val Leu Tyr Ala Ala Pro Leu Ser Pro Leu
     50                  55                  60 cta ccc ctc cag gac ggc acc aat act cat ata atg gcc aca gaa gct        241
Leu Pro Leu Gln Asp Gly Thr Asn Thr His Ile Met Ala Thr Glu Ala
 65                  70                  75                  80 tct aat tat gcc cag tac cgg gtt gct cgt gcc aca att cgc tac cgc        289
Ser Asn Tyr Ala Gln Tyr Arg Val Ala Arg Ala Thr Ile Arg Tyr Arg
                 85                  90                  95 ccg ctg gtc ccc aac gct gtt ggt ggc tac gcc atc tcc atc tcg ttc        337
Pro Leu Val Pro Asn Ala Val Gly Gly Tyr Ala Ile Ser Ile Ser Phe
             100                 105                 110 tgg cca cag acc acc acc acc ccg acg tcc gtt gac atg aat tca ata        385
Trp Pro Gln Thr Thr Thr Thr Pro Thr Ser Val Asp Met Asn Ser Ile
         115                 120                 125 acc tcg acg gat gtt cgt att tta gtc cag ccc ggc ata gcc tcc gag        433
Thr Ser Thr Asp Val Arg Ile Leu Val Gln Pro Gly Ile Ala Ser Glu
     130                 135                 140 ctt gtt atc cca agt gag cgc cta cac tac cgt aac caa ggt tgg cgc        481
Leu Val Ile Pro Ser Glu Arg Leu His Tyr Arg Asn Gln Gly Trp Arg
145                 150                 155                 160 tct gtt gag acc tcc ggg gtg gcg gag gag gag gcc acc tct ggt ctt        529
Ser Val Glu Thr Ser Gly Val Ala Glu Glu Glu Ala Thr Ser Gly Leu
                 165                 170                 175 gtt atg ctc tgc ata cat ggc tca cct gta aat tct tat act aat aca        577
Val Met Leu Cys Ile His Gly Ser Pro Val Asn Ser Tyr Thr Asn Thr
             180                 185                 190 cct tat acc ggt gcc ctc ggg ctg ttg gac ttt gcc ctc gaa ctt gag        625
Pro Tyr Thr Gly Ala Leu Gly Leu Leu Asp Phe Ala Leu Glu Leu Glu
         195                 200                 205 ttc cgc aac ctc acc ccc ggt aat acc aac acg cgg gtc tcc cgt tac        673
Phe Arg Asn Leu Thr Pro Gly Asn Thr Asn Thr Arg Val Ser Arg Tyr
     210                 215                 220 tcc agc act gcc cgt cac cgc ctt cgt cgc ggt gca gat ggg act gcc        721
Ser Ser Thr Ala Arg His Arg Leu Arg Arg Gly Ala Asp Gly Thr Ala
225                 230                 235                 240 gag ctt acc acc acg gct gct acc cgc ttc atg aag gac ctc tat ttt        769
Glu Leu Thr Thr Thr Ala Ala Thr Arg Phe Met Lys Asp Leu Tyr Phe
                 245                 250                 255 act agt act aat ggt gtc ggt gag atc ggc cgt ggg ata gcg ctt acc        817
Thr Ser Thr Asn Gly Val Gly Glu Ile Gly Arg Gly Ile Ala Leu Thr
             260                 265                 270 ctg ttt aac ctt gct gac acc ctg ctt ggc ggt cta ccg aca gaa ttg        865
Leu Phe Asn Leu Ala Asp Thr Leu Leu Gly Gly Leu Pro Thr Glu Leu
         275                 280                 285 att tcg tcg gct ggt ggc cag ctg ttc tac tct cgt ccc gtc gtc tca        913
Ile Ser Ser Ala Gly Gly Gln Leu Phe Tyr Ser Arg Pro Val Val Ser
     290                 295                 300
```

-continued

| | |
|---|---|
| gcc aat ggc gag ccg act gtt aag ctt tat aca tct gta gag aat gct<br>Ala Asn Gly Glu Pro Thr Val Lys Leu Tyr Thr Ser Val Glu Asn Ala<br>305                    310                    315                    320 | 961 |
| cag cag gat aag ggt att gca atc ccg cat gac atc gac ctc ggg gag<br>Gln Gln Asp Lys Gly Ile Ala Ile Pro His Asp Ile Asp Leu Gly Glu<br>                  325                    330                    335 | 1009 |
| tct cgt gta gtt att cag gat tat gac aac caa cat gag cag gac cga<br>Ser Arg Val Val Ile Gln Asp Tyr Asp Asn Gln His Glu Gln Asp Arg<br>              340                    345                    350 | 1057 |
| ccg aca cct tcc cca gcc cca tcg cgc cct ttt tct gtc ctc cga gct<br>Pro Thr Pro Ser Pro Ala Pro Ser Arg Pro Phe Ser Val Leu Arg Ala<br>        355                    360                    365 | 1105 |
| aat gat gtg ctt tgg ctt tct ctc acc gct gcc gag tat gac cag tcc<br>Asn Asp Val Leu Trp Leu Ser Leu Thr Ala Ala Glu Tyr Asp Gln Ser<br>370                    375                    380 | 1153 |
| act tac ggc tct tcg acc ggc cca gtc tat gtc tct gac tct gtg acc<br>Thr Tyr Gly Ser Ser Thr Gly Pro Val Tyr Val Ser Asp Ser Val Thr<br>385                    390                    395                    400 | 1201 |
| ttg gtt aat gtt gcg acc ggc gcg cag gcc gtt gcc cgg tca ctc gac<br>Leu Val Asn Val Ala Thr Gly Ala Gln Ala Val Ala Arg Ser Leu Asp<br>                  405                    410                    415 | 1249 |
| tgg acc aag gtc aca ctt gat ggt cgc ccc ctt tcc acc atc cag cag<br>Trp Thr Lys Val Thr Leu Asp Gly Arg Pro Leu Ser Thr Ile Gln Gln<br>        420                    425                    430 | 1297 |
| tat tca aag acc ttc ttt gtc ctg ccg ctc cgc ggt aag ctc tcc ttt<br>Tyr Ser Lys Thr Phe Phe Val Leu Pro Leu Arg Gly Lys Leu Ser Phe<br>435                    440                    445 | 1345 |
| tgg gag gca ggt act act aaa gcc ggg tac cct tat aat tat aac acc<br>Trp Glu Ala Gly Thr Thr Lys Ala Gly Tyr Pro Tyr Asn Tyr Asn Thr<br>450                    455                    460 | 1393 |
| act gct agt gac caa ctg ctc gtt gag aat gcc gct ggg cat cgg gtt<br>Thr Ala Ser Asp Gln Leu Leu Val Glu Asn Ala Ala Gly His Arg Val<br>465                    470                    475                    480 | 1441 |
| gct att tcc act tac acc act agc ctg ggt gct ggt ccc gtc tct att<br>Ala Ile Ser Thr Tyr Thr Thr Ser Leu Gly Ala Gly Pro Val Ser Ile<br>                  485                    490                    495 | 1489 |
| tcc gcg gtt gct gtt tta gcc ccc cac tcc gcg cta gca ttg ctt gag<br>Ser Ala Val Ala Val Leu Ala Pro His Ser Ala Leu Ala Leu Leu Glu<br>        500                    505                    510 | 1537 |
| gat acc atg gac tac cct gcc cgc gcc cat act ttc gat gac ttc tgc<br>Asp Thr Met Asp Tyr Pro Ala Arg Ala His Thr Phe Asp Asp Phe Cys<br>515                    520                    525 | 1585 |
| ccg gag tgc cgc ccc ctt ggc ctc cag ggc tgt gct ttt cag tct act<br>Pro Glu Cys Arg Pro Leu Gly Leu Gln Gly Cys Ala Phe Gln Ser Thr<br>530                    535                    540 | 1633 |
| gtc gct gag ctt cag cgc ctt aag atg aag gtg ggt aaa act cgg gag<br>Val Ala Glu Leu Gln Arg Leu Lys Met Lys Val Gly Lys Thr Arg Glu<br>545                    550                    555                    560 | 1681 |
| tta ta<br>Leu | 1686 |

<210> SEQ ID NO 20
<211> LENGTH: 561
<212> TYPE: PRT
<213> ORGANISM: Homo sapiens

<400> SEQUENCE: 20

Arg Arg Pro Thr Thr Ala Gly Ala Ala Pro Leu Thr Ala Val Ala Pro
1                 5                    10                    15

-continued

```
Ala His Asp Thr Pro Val Pro Asp Val Asp Ser Arg Gly Ala Ile
             20              25              30

Leu Arg Arg Gln Tyr Asn Leu Ser Thr Ser Pro Leu Thr Ser Ser Val
         35              40              45

Ala Thr Gly Thr Asn Leu Val Leu Tyr Ala Ala Pro Leu Ser Pro Leu
     50              55              60

Leu Pro Leu Gln Asp Gly Thr Asn Thr His Ile Met Ala Thr Glu Ala
 65              70              75              80

Ser Asn Tyr Ala Gln Tyr Arg Val Ala Arg Ala Thr Ile Arg Tyr Arg
             85              90              95

Pro Leu Val Pro Asn Ala Val Gly Gly Tyr Ala Ile Ser Ile Ser Phe
         100             105             110

Trp Pro Gln Thr Thr Thr Thr Pro Thr Ser Val Asp Met Asn Ser Ile
         115             120             125

Thr Ser Thr Asp Val Arg Ile Leu Val Gln Pro Gly Ile Ala Ser Glu
     130             135             140

Leu Val Ile Pro Ser Glu Arg Leu His Tyr Arg Asn Gln Gly Trp Arg
145             150             155             160

Ser Val Glu Thr Ser Gly Val Ala Glu Glu Ala Thr Ser Gly Leu
             165             170             175

Val Met Leu Cys Ile His Gly Ser Pro Val Asn Ser Tyr Thr Asn Thr
         180             185             190

Pro Tyr Thr Gly Ala Leu Gly Leu Leu Asp Phe Ala Leu Glu Leu Glu
     195             200             205

Phe Arg Asn Leu Thr Pro Gly Asn Thr Asn Thr Arg Val Ser Arg Tyr
 210             215             220

Ser Ser Thr Ala Arg His Arg Leu Arg Arg Gly Ala Asp Gly Thr Ala
225             230             235             240

Glu Leu Thr Thr Thr Ala Ala Thr Arg Phe Met Lys Asp Leu Tyr Phe
             245             250             255

Thr Ser Thr Asn Gly Val Gly Glu Ile Gly Arg Gly Ile Ala Leu Thr
         260             265             270

Leu Phe Asn Leu Ala Asp Thr Leu Gly Gly Leu Pro Thr Glu Leu
     275             280             285

Ile Ser Ser Ala Gly Gly Gln Leu Phe Tyr Ser Arg Pro Val Val Ser
 290             295             300

Ala Asn Gly Glu Pro Thr Val Lys Leu Tyr Thr Ser Val Glu Asn Ala
305             310             315             320

Gln Gln Asp Lys Gly Ile Ala Ile Pro His Asp Ile Asp Leu Gly Glu
             325             330             335

Ser Arg Val Val Ile Gln Asp Tyr Asp Asn Gln His Glu Gln Asp Arg
         340             345             350

Pro Thr Pro Ser Pro Ala Pro Ser Arg Pro Phe Ser Val Leu Arg Ala
     355             360             365

Asn Asp Val Leu Trp Leu Ser Leu Thr Ala Ala Glu Tyr Asp Gln Ser
 370             375             380

Thr Tyr Gly Ser Ser Thr Gly Pro Val Tyr Val Ser Asp Ser Val Thr
385             390             395             400

Leu Val Asn Val Ala Thr Gly Ala Gln Ala Val Ala Arg Ser Leu Asp
             405             410             415

Trp Thr Lys Val Thr Leu Asp Gly Arg Pro Leu Ser Thr Ile Gln Gln
         420             425             430
```

| | | | | | | | | | | | |
|---|---|---|---|---|---|---|---|---|---|---|---|
|Tyr|Ser|Lys|Thr|Phe|Phe|Val|Leu|Pro|Leu|Arg|Gly|Lys|Leu|Ser|Phe|
| |435| | | | |440| | | |445| |

Tyr Ser Lys Thr Phe Phe Val Leu Pro Leu Arg Gly Lys Leu Ser Phe
            435                 440                 445

Trp Glu Ala Gly Thr Thr Lys Ala Gly Tyr Pro Tyr Asn Tyr Asn Thr
            450                 455                 460

Thr Ala Ser Asp Gln Leu Leu Val Glu Asn Ala Ala Gly His Arg Val
465                 470                 475                 480

Ala Ile Ser Thr Tyr Thr Thr Ser Leu Gly Ala Gly Pro Val Ser Ile
            485                 490                 495

Ser Ala Val Ala Val Leu Ala Pro His Ser Ala Leu Ala Leu Leu Glu
            500                 505                 510

Asp Thr Met Asp Tyr Pro Ala Arg Ala His Thr Phe Asp Asp Phe Cys
            515                 520                 525

Pro Glu Cys Arg Pro Leu Gly Leu Gln Gly Cys Ala Phe Gln Ser Thr
            530                 535                 540

Val Ala Glu Leu Gln Arg Leu Lys Met Lys Val Gly Lys Thr Arg Glu
545                 550                 555                 560

Leu

<210> SEQ ID NO 21
<211> LENGTH: 331
<212> TYPE: DNA
<213> ORGANISM: Homo sapiens
<220> FEATURE:
<221> NAME/KEY: CDS
<222> LOCATION: (1)..(330)

<400> SEQUENCE: 21

```
atg cgc cct cgg cct att ttg ctg ttg ctc ctc atg ttt ctg cct atg        48
Met Arg Pro Arg Pro Ile Leu Leu Leu Leu Leu Met Phe Leu Pro Met
1               5                   10                  15 ctg ccc gcg cca ccg ccc ggt cag ccg tct ggc cgc cgt cgt ggg cgg        96
Leu Pro Ala Pro Pro Pro Gly Gln Pro Ser Gly Arg Arg Arg Gly Arg
            20                  25                  30 cgc agc ggc ggt tcc ggc ggt ggt ttc tgg ggt gac cgg gtt gat tct       144
Arg Ser Gly Gly Ser Gly Gly Gly Phe Trp Gly Asp Arg Val Asp Ser
        35                  40                  45 cag ccc ttc gca atc ccc tat att cat cca acc aac ccc ttc gcc ccc       192
Gln Pro Phe Ala Ile Pro Tyr Ile His Pro Thr Asn Pro Phe Ala Pro
    50                  55                  60 gat gtc acc gct gcg gcc ggg gct gga cct cgt gtt cgc caa ccc gcc       240
Asp Val Thr Ala Ala Ala Gly Ala Gly Pro Arg Val Arg Gln Pro Ala
65                  70                  75                  80 cga cca ctc ggc tcc gct tgg cgt gac cag gcc cag cgc ccc gcc gtt       288
Arg Pro Leu Gly Ser Ala Trp Arg Asp Gln Ala Gln Arg Pro Ala Val
                85                  90                  95 gcc tca cgt cgt aga cct acc aca gct ggg gcc gcg ccg cta a             331
Ala Ser Arg Arg Arg Pro Thr Thr Ala Gly Ala Ala Pro Leu
                100                 105                 110
```

<210> SEQ ID NO 22
<211> LENGTH: 110
<212> TYPE: PRT
<213> ORGANISM: Homo sapiens

<400> SEQUENCE: 22

Met Arg Pro Arg Pro Ile Leu Leu Leu Leu Leu Met Phe Leu Pro Met
1               5                   10                  15

Leu Pro Ala Pro Pro Pro Gly Gln Pro Ser Gly Arg Arg Arg Gly Arg
            20                  25                  30

```
Arg Ser Gly Gly Ser Gly Gly Gly Phe Trp Gly Asp Arg Val Asp Ser
         35                  40                  45

Gln Pro Phe Ala Ile Pro Tyr Ile His Pro Thr Asn Pro Phe Ala Pro
     50                  55                  60

Asp Val Thr Ala Ala Ala Gly Ala Gly Pro Arg Val Arg Gln Pro Ala
 65                  70                  75                  80

Arg Pro Leu Gly Ser Ala Trp Arg Asp Gln Ala Gln Arg Pro Ala Val
             85                  90                  95

Ala Ser Arg Arg Arg Pro Thr Thr Ala Gly Ala Ala Pro Leu
            100                 105                 110
```

<210> SEQ ID NO 23
<211> LENGTH: 672
<212> TYPE: DNA
<213> ORGANISM: Homo sapiens
<220> FEATURE:
<221> NAME/KEY: CDS
<222> LOCATION: (1)..(672)

<400> SEQUENCE: 23

```
atg cgc cct cgg cct att ttg ctg ttg ctc ctc atg ttt ctg cct atg        48
Met Arg Pro Arg Pro Ile Leu Leu Leu Leu Leu Met Phe Leu Pro Met
  1               5                  10                  15 ctg ccc gcg cca ccg ccc ggt cag ccg tct ggc cgc cgt cgt ggg cgg        96
Leu Pro Ala Pro Pro Pro Gly Gln Pro Ser Gly Arg Arg Arg Gly Arg
             20                  25                  30 cgc agc ggc ggt tcc ggc ggt ggt ttc tgg ggt gac cgg gtt gat tct       144
Arg Ser Gly Gly Ser Gly Gly Gly Phe Trp Gly Asp Arg Val Asp Ser
         35                  40                  45 cag ccc ttc gca atc ccc tat att cat cca acc aac ccc ttc gcc ccc       192
Gln Pro Phe Ala Ile Pro Tyr Ile His Pro Thr Asn Pro Phe Ala Pro
     50                  55                  60 gat gtc acc gct gcg gcc ggg gct gga cct cgt gtt cgc caa ccc gcc       240
Asp Val Thr Ala Ala Ala Gly Ala Gly Pro Arg Val Arg Gln Pro Ala
 65                  70                  75                  80 cga cca ctc ggc tcc gct tgg cgt gac cag gcc cag cgc ccc gcc gtt       288
Arg Pro Leu Gly Ser Ala Trp Arg Asp Gln Ala Gln Arg Pro Ala Val
             85                  90                  95 gcc tca cgt cgt aga cct acc aca gct ggg gcc gcg ccg cta acc gcg       336
Ala Ser Arg Arg Arg Pro Thr Thr Ala Gly Ala Ala Pro Leu Thr Ala
            100                 105                 110 gtc gct ccg gcc cat gac acc ccg cca gtg cct gat gtt gac tcc cgc       384
Val Ala Pro Ala His Asp Thr Pro Pro Val Pro Asp Val Asp Ser Arg
        115                 120                 125 ggc gcc atc ctg cgc cgg cag tat aac cta tca aca tct ccc ctt act       432
Gly Ala Ile Leu Arg Arg Gln Tyr Asn Leu Ser Thr Ser Pro Leu Thr
130                 135                 140 tct tcc gtg gcc acc ggt aca aac ttg gtt cta tac gcc gct cct ctt       480
Ser Ser Val Ala Thr Gly Thr Asn Leu Val Leu Tyr Ala Ala Pro Leu
145                 150                 155                 160 agc cca ctt cta ccc ctc cag gac ggc acc aat act cat ata atg gcc       528
Ser Pro Leu Leu Pro Leu Gln Asp Gly Thr Asn Thr His Ile Met Ala
                165                 170                 175 aca gaa gct tct aat tat gcc cag tac cgg gtt gct cgt gcc aca att       576
Thr Glu Ala Ser Asn Tyr Ala Gln Tyr Arg Val Ala Arg Ala Thr Ile
            180                 185                 190 cgc tac cgc ccg ctg gtc ccc aac gct gtt ggt ggc tac gcc atc tcc       624
Arg Tyr Arg Pro Leu Val Pro Asn Ala Val Gly Gly Tyr Ala Ile Ser
        195                 200                 205
```

```
atc tcg ttc tgg cca cag acc acc acc acc ccg acg tcc gtt gac atg      672
Ile Ser Phe Trp Pro Gln Thr Thr Thr Thr Pro Thr Ser Val Asp Met
    210                 215                 220
```

<210> SEQ ID NO 24
<211> LENGTH: 224
<212> TYPE: PRT
<213> ORGANISM: Homo sapiens

<400> SEQUENCE: 24

```
Met Arg Pro Arg Pro Ile Leu Leu Leu Leu Met Phe Leu Pro Met
 1               5                  10                  15

Leu Pro Ala Pro Pro Gly Gln Pro Ser Gly Arg Arg Arg Gly Arg
                20                  25                  30

Arg Ser Gly Gly Ser Gly Gly Gly Phe Trp Gly Asp Arg Val Asp Ser
            35                  40                  45

Gln Pro Phe Ala Ile Pro Tyr Ile His Pro Thr Asn Pro Phe Ala Pro
    50                  55                  60

Asp Val Thr Ala Ala Gly Ala Gly Pro Arg Val Arg Gln Pro Ala
 65                 70                  75                  80

Arg Pro Leu Gly Ser Ala Trp Arg Asp Gln Ala Gln Arg Pro Ala Val
                85                  90                  95

Ala Ser Arg Arg Arg Pro Thr Thr Ala Gly Ala Ala Pro Leu Thr Ala
                100                 105                 110

Val Ala Pro Ala His Asp Thr Pro Pro Val Pro Asp Val Asp Ser Arg
                115                 120                 125

Gly Ala Ile Leu Arg Arg Gln Tyr Asn Leu Ser Thr Ser Pro Leu Thr
    130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
                180                 185                 190

Arg Tyr Arg Pro Leu Val Pro Asn Ala Val Gly Gly Tyr Ala Ile Ser
    195                 200                 205

Ile Ser Phe Trp Pro Gln Thr Thr Thr Thr Pro Thr Ser Val Asp Met
    210                 215                 220
```

IMMUNOREACTIVE ANTIGENS OF HEPATITIS E VIRUS

This application is a continuation-in-part of U.S. Ser. No. 08/617,927 filed on Mar. 22, 1996, now abandoned, which is a U.S. National stage application under 35 U.S.C. §371 of international application PCT/AU94/00572, filed Sep. 23, 1994.

The present invention relates generally to molecules such as peptides, polypeptides and proteins which carry epitopes and in particular B cell epitopes from antigenic proteins encoded by Hepatitis E Virus. These molecules are preferentially immunoreactive to convalescent or acute phase circulating antibodies to the Hepatitis E Virus and are useful in the development of diagnostic, therapeutic and prophylactic agents for Hepatitis E Virus.

Bibliographic details of the publications referred to by author in this specification are collected at the end of the description. Sequence Identity Numbers (SEQ ID NOs.) for the nucleotide and amino acid sequences referred to in the specification are defined following the bibliography.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Viral hepatitis results from infection with one of at least five very different viral agents. Available serological tests allow the diagnosis of acute hepatitis due to infection with Hepatitis A Virus (HAV) and Hepatitis B Virus (HBV). HBV is required for propagation of the delta agent, or Hepatitis D Virus (HDV); this co-infection results in a high proportion of cases progressing to chronic active hepatitis. The clinical and diagnostic exclusion of HAV and HBV has led to the recognition of other hepatitides that were formerly grouped together as non-A, non-B hepatitis [(NANBH)] (Prince et al., 1974; Feinstone et al., 1975; Tabor, 1985). NANBH is caused by more than one viral agent and can be transmitted by either parenteral or fecal/oral routes (Bradley, 1990a; Reyes and Baroudy, 1991).

The cloning of a blood-borne agent, termed Hepatitis C Virus (HCV), led to the development of a specific assay for circulating antibody to HCV (Choo et al., 1989; Kuo et al., 1989; Kubo et al., 1989, Maeno et al., 1990). This assay predominantly detects infections at the chronic stage, but has facilitated the identification of HCV as the cause of up to 90% of parenterally transmitted NANBH. A second epidemiologically distinct form of NANBH has been shown to occur in both epidemic and sporadic patterns in developing countries and is referred to as enterically transmitted non-A, non-B hepatitis (ET-NANBH) due to its water-borne mode of virus transmission and presumed enteric route of infection (Khuroo, 1980; Wong et al., 1980). ET-NANBH has been documented in India, Pakistan, Burma, USSR, Costa Rica, Mexico and countries in Africa where epidemic outbreaks can generally be traced to fecal contamination of drinking water (Bradley and Maynard, 1986; Bradley, 1990b). The causative viral agent was previously shown to passage successfully in cynomolgus macaques (cyno) and tamarins with typical liver enzyme elevations and recovery of morphologically similar 27 to 34 mm virus like particles from the feces of clinical specimens and experimental animals (Balayan et al., 1983; Andiaparidze et al., 1986; Bradley et al., 1987; Arankalle et al., 1988).

Reyes et al. (1990) recently reported the isolation of a partial cDNA clone from the virus responsible for ET-NANBH, and termed the newly identified agent the Hepatitis E Virus (HEV). The expressions "enterically transmitted non-A, non-B hepatitis", "ET-NANBH", "Hepatitis E Virus" and "HEV" are used interchangeably herein to refer to a virus or type of virus which is capable of causing infectious hepatitis from contaminated water, which is transmissible and capable of passage in cynomologus macaques and tramarins, which is serologically distinct from HAV, HBV, HCV and HDV and which comprises a genomic nucleotide sequence, a portion of which, at least is homologous to or substantially similar to or capable of hybridizing under low stringency conditions to the all or part of the nucleotide sequences set forth in FIG. 1 and/or FIG. 2. Preferred homologies and a definition of stringency conditions are set forth below.

The HEV clone was from a Burma isolate of the virus and hybridised with cDNA made from five other distinct geographic isolates. These molecular epidemiological findings are consistent with the available serologic data based on the use of immune electron microscopy and imunofluorescence blocking studies that indicate a single major agent is responsible for the majority of ET-NANBH seen worldwide (Purcell and Ticehurst, 1988; Bradley et al. 1988a; Krawczynski and Bradley, 1989). Tam et al. (1991) subsequently reported on the molecular cloning of the complete HEV (Burma; B) viral clone together with the deduced amino acid sequences.

HEV has a single stranded genome of polyadenylated RNA of positive polarity which encodes three open reading frames (ORF's) designated ORF1, ORF2 and ORF3. Open reading frame 2 and ORF3 are partially overlapping in different reading frames and are thought to encode structural proteins of the virus. Open reading frame 1, on the other hand, encodes replicative proteins and overlaps ORF3 by one nucleotide.

Despite the availability of immunoassays for the detection of antibodies to some strains of HEV, it has been observed that IgM and IgG antibody titres wane rapidly following infection. Consequently, it has proven difficult to interpret serological surveys from both endemic and non-endemic areas. Furthermore, the relationship between antibody interactivity and immunity to reinfection remains unclear. These and other factors have delayed the development of suitable diagnostic and therapeutic protocols for the HEV, for which a need clearly exists. In particular, it would be most beneficial to develop an assay which could distinguish between acute phase antibodies (contemporary antibodies) generated in response to HEV infection and convalescent phase antibodies, which remain in the circulatory and/or secretory system after infection and may contribute to immunity to reinfection.

In work leading up to the present invention, the inventors sought to identify epitopes, and in particular B cell epitopes, on peptides, polypeptides and proteins encoded within the HEV genome in order to improve upon current diagnostic procedures and to further develop therapeutic and prophylactic compositions for HEV. In accordance with the present invention, peptides, polypeptides and proteins, were recombinantly expressed from nucleic acid molecules derived from ORFs in the HEV genome. The epitopic and in particular B cell epitopic regions within these molecules were identified on the basis of interactivity to antibodies specific to HEV, thereby forming the basis for a new range of diagnostic, therapeutic and prophylactic procedures for HEV. Interestingly, the inventors have determined that one portion of a molecule encoded by an ORF may inhibit or otherwise reduce the immunointeractivity of another portion of the same molecule. They have further determined that the inhibitory effect may be overcome by using non-full length molecules or reducing the inhibitory effect by physical or chemical processes.

Accordingly, one aspect of the present invention provides a recombinant molecule encoded by a sequence of nucleotides selected from the list consisting of open reading frame (ORF) 2 and ORF 3 of Hepatitis E Virus (HEV) or a mutant or derivative of said ORF2 or ORF3. More particularly, the present invention provides a recombinant molecule encoded by a sequence of nucleotides comprising "ORF3" or a part of "ORF2" and which molecule is preferentially immunologically interactive in either convalescent phase or acute phase antibodies to HEV are conveniently described respectively as those regions of the HEV genome beginning at nucleotide 5106 extending 369 bases and terminating at nucleotide 5474 (ORF3) and that region beginning at nucleotide 5147 extending 1980 bases and terminating 68 bases upstream of the poly(A) tail (ORF2) using the numbering system of Tam et al. (1991).

The term "recombinant molecule" in this context includes a peptide, polypeptide, protein or a chemical equivalent thereof. The recombinant molecule may or may not be glycosylated. A recombinant molecule also extends to a fusion between an HEV derived peptide, polypeptide or protein and a peptide, polypeptide or protein of non-HEV origin such as but not limited to glutathione-S-transferase (GST) or its derivatives, polylysine, polyhistidine, thioredoxin or any other molecule capable of bioaffinity chromatography.

In accordance with the present invention, it has been surprisingly discovered that recombinant molecules encoded by ORF2 and in particular the 3' end of ORF2 and ORF3 are capable of interacting with convalescent phase antibodies to HEV whereas recombinant molecules encoded by the 5' end of ORF2 are interactive more preferentially with acute phase antibodies generated to the virus particle per se. According to this aspect of the present invention, there is provided a recombinant peptide or polypeptide which is preferentially immunologically reactive with convalescent phase antibodies generated during HEV infection. In a related aspect of the present invention, there is provided a recombinant peptide or polypeptide which is preferentially immunologically interactive with acute phase antibodies generated during HEV infection.

As used herein, the 3' end of an ORF (e.g. ORF2) is considered the carboxy (C)-terminal end portion of the molecule encoded by the ORF and the 5' end is considered the amino (N)-terminal end portion.

More particularly, it has further been surprisingly discovered that the 5' (i.e. the C-terminal) end portion of ORF2 exhibits greater immunointeractivity to acute phase antibodies to HEV and the 5' (i.e. N-terminal) end portion of ORF2 exhibits greater immunointeractivity to convalescent phase antibodies to HEV, when present on the same molecule, however, the N-terminal end portion appears to inhibit or reduce the immunointeractivity of the C-terminal end portion.

Accordingly, another aspect of the present invention contemplates a recombinant molecule encoded by a sequence of nucleotides comprising ORF3 or a non-full length ORF2 derived from the 3' end of ORF2 of HEV and wherein said recombinant molecule is preferentially interactive with convalescent phase antibodies to HEV. In a related aspect there is provided a recombinant molecule encoded by a sequence of nucleotides comprising a non-length ORF2 derived from the 5' end of ORF2 of HEV and wherein said recombinant molecule is preferentially interactive with acute phase antibodies to HEV.

In one embodiment the sequence of nucleotides is from the 5' end of ORF2 and encodes a molecule more interactive with acute phase antibodies relative to convalescent phase antibodies. In another embodiment, the nucleotide sequence is from ORF3 or the 3' end of ORF2 and encodes a molecule more interactive with convalescent phase antibodies relative to acute phase antibodies. The preferred nucleotide sequence of the 5' end of ORF2 includes the clones 2.3 and 2.4 defined in FIG. 5.

The recombinant molecule may also be encoded by a nucleotide sequence comprising the full length ORF2 but modified to permit interactivity to both convalescent and acute phase antibodies to HEV. Such modification includes chemical and physical treatments to expose epitopes, for example by denaturing followed by renaturing of the molecule or the use of antagonists to prevent the inhibition of, for example, the N-terminal end portion over the C-terminal end portion binding to HEV antibodies.

"Acute and "convalescent" phases are used in their broadest sense to mean respectively the period during infection (acute) and the period beginning from after the peak of infection extending through a convalescent period to a period post infection. The acute phase of infection can conveniently be considered, for example, to be approximately 3 to 6 months following exposure to HEV and the convalescent phase is generally after this period.

Yet another aspect of the present invention is directed to a recombinant polypeptide comprising first and second amino acid sequences wherein said first amino acid sequence is encoded by a nucleotide sequence selected from or within ORF2 and ORF 3 of HEV and wherein said second amino acid sequence is a non-HEV encoded peptide, polypeptide or protein such as but not exclusively GST. Preferably, the first amino acid sequence is encoded by ORF3 or the 3' end of ORF2 and is interactive with convalescent phase antibodies to HEV. Alternatively, the first amino acid sequence is from the 5' end portion of ORF2 and is preferably interactive with acute phase antibodies to HEV.

The presence of selectively or preferentially immunologically reactive antigens provides a means of distinguishing between past (convalescent) and acute (contemporary) phase infection with HEV. Accordingly, the present invention also extends to a method for distinguishing between convalescent and acute phase infection with HEV in an individual which method measures the reactivity of serum to immune interactive recombinant molecule encoded by ORF2 and/or ORF3 or more preferably parts thereof. Most preferably, these parts include the 3' end portion of ORF2 or the 5' end portion of ORF2 or is a chemically modified form of a fill length molecule such as to expose epitopes on both the N- and C-termini.

The present invention also provides an isolated nucleic acid molecule such as DNA or eDNA molecule comprising a sequence of nucleotides encoding or complementary to a sequence encoding a peptide, polypeptide or protein interactive with acute phase antibodies to HEV. In an alternative embodiment, the peptide, polypeptide or protein is interactive with both convalescent and/or acute phase circulating antibodies to HEV. Accordingly, this aspect of the present invention provides a recombinant molecule carrying a B cell epitope of a polypeptide or protein encoded by ORF2 or ORF3 or more preferably a part thereof. More particularly, the sequence of nucleotides is selected from a sequence comprising or within nucleotides 5147 to 7129 (ORF2) and 5106 to 5474 (ORF3) in the HEV genome using the nucleotide numbering system of Tam et al (1991) or a nucleotide region substantially equivalent thereto. Preferably, the nucleotide sequence is operably linked to an expression control sequence such as in the form of an expression vector.

The recombinant molecule according to this aspect of the present invention is generally an isolated nucleic acid molecule comprising DNA (eg cDNA or genonic DNA) or mRNA. The recombinant molecule may be isolated directly from the HEV genome or may be generated in vitro by, for example, the stepwise addition of nucleotides or groups of nucleotides. The present invention further extends to a host cell such as bacterium, yeast, mammalian or insect cell transformed with such a recombinant molecule. A preferred mammalian cell is the Chinese Hamster Ovary (CHO) cell line. A preferred bacterium is E. coli. Preferably, the nucleic acid molecules are DNA, at least parts of which have a nucleotide sequence substantially corresponding to all or part of the nucleotide sequence shown in FIGS. 1 (SEQ ID NO: 1) or 2 (SEQ ID NO: 3) or a part, fragment, derivative, homologue or analogue thereof or one or more sequences complementary thereto. The present invention, however also extends to any single or multiple nucleotide substitutions, deletions and/or additions to the sequence shown in FIGS. 1 or 2 and which still encode an epitopic region of the HEV genome or fragment or derivative thereof having the requisite antigenic profile and interactive with antibodies to HEV. Most preferably, the nucleotide sequence encode either the 3' end of ORF2 or the 5' end of ORF2 such that the nucleotide sequence encodes a peptide or polypeptide which interacts preferably with convalescent phase antibodies or acute phase antibodies, respectively.

Furthermore, when the nucleic acid molecule is RNA, the ribonucleotide sequence will, in a preferred embodiment, be substantially complementary to one or more of the nucleotide sequences shown in FIGS. 1 or 2 a part, fragment, derivative, homologue or analogue thereof. Another aspect of this invention is directed to a synthetic (e.g. recombinant) peptide, polypeptide or protein which is immunologically interactive with convalescent phase antibodies generating during HEV infection. Furthermore, the invention is further directed to a synthetic (eg: recombinant) peptide, polypeptide or protein which is immunologically interactive with acute and convalescent circulating antibodies generated during HEV infection.

Such synthetic peptides, polypeptides or proteins may, for example, be prepared by recombinant means such as by the expression of a host cell transformed with the recombinant molecules described above. The peptide, polypeptide or protein may be fused to another peptide, polypeptide or protein. Alternatively, it may be prepared by chemical synthesis, such as by the Merrifield solid-phase synthesis procedure. Furthermore, although synthetic or fragments thereof represent a preferred embodiment, the present invention also extends to biologically pure preparations of the naturally occurring epitopes or their fragments. By "biologically pure" is meant a preparation of at least 60%, preferably at least 70%, more preferably at least 80% and still more preferably at least 90% by weight peptide, polypeptide or protein.

Another aspect of the present invention contemplates a peptide, polypeptide or protein carrying a B cell epitope interactive with antibodies to HEV, said peptide, polypeptide or protein being encoded by a sequence of nucleotides capable of hybridising under low stringency conditions to one or more regions of the nucleotide sequence set forth in FIG. 1 (SEQ ID NO: 1) or 2 (SEQ ID NO: 3).

More particularly, one aspect of this embodiment is directed to a nucleic acid molecule comprising a sequence of nucleotides which:

(i) encodes a peptide, polypeptide or protein interactive with acute and/or convalescent phase antibodies to HEV; and (ii) is capable of hybridizing under low stringency conditions to all or part of the nucleotide sequence set forth in FIG. 1 (SEQ ID NO: 1) under low stringency conditions.

In a related aspect, the nucleotide sequence encodes a peptide, polypeptide or protein interactive with acute phase antibodies and is capable of hybridizing under low stringency conditions to all or part of the nucleotide sequence set forth in FIG. 1 or FIG. 2.

In a preferred embodiment, the nucleotide sequence is capable of hybridizing to the 5' end of ORF2 and encodes a molecule capable of preferential interaction with acute phase antibodies to HEV. Most preferably, the nucleotide sequence is sequence 2.3 or 2.4 of FIG. 5.

Another aspect of this embodiment of the present invention provides a recombinant peptide, polypeptide or protein encoded by a nucleotide sequence capable of hybridizing under low stringency conditions to all or part of the nucleotide sequence set forth in FIG. 1 (SEQ ID NO: 1) or FIG. 2 (SEQ ID NO: 3). This aspect of the present invention includes recombinant or synthetic forms of naturally occurring proteins encoded by the aforementioned nucleotide sequences as well as peptide, polypeptide or protein derivatives thereof which are encoded by modified nucleotide sequences still capable of hybridizing to the nucleotide sequence in FIG. 1 (SEQ ID NO: 1) or 2 (SEQ ID NO: 3) and which derivatives are interactive with acute and/or convalescent phase antibodies to HEV.

For the purposes of defining the level of stringency, reference can conveniently be made to Maniatis et al (1982) at pages 387–389 which is herein incorporated by reference where the washing step disclosed is considered high stringency. A low stringency is defined herein as being in 4–6×SSC/0.1–0.5% w/v SDS at 37–45° C. for 2–3 hours. Depending on the source and concentration of nucleic acid involved in the hybridization, alternative conditions of stringency may be employed such as medium stringent conditions which are considered herein to be 1–4×SSC/0.25–0.5% w/v SDS at $\geq$45° C. for 2–3 hours or high stringency conditions which are considered herein to be 0.1–1×SSC/0.1% w/v SDS at $\geq$60° C. for 1–3 hours.

In yet a further aspect, the present invention contemplates a peptide, polypeptide or protein carrying a B cell epitope interactive with antibodies to HEV, said peptide, polypeptide or protein having a substantially similar amino acid sequence to one or more regions of the amino acid sequences set forth in FIG. 1 (SEQ ID NO: 2) or 2 (SEQ ID NO: 4). By "substantially similar" is meant a sequence having at least 50%, preferably at least 60%, more preferably at least 75% and still more preferably at least 90% homology (i.e. similarity) with the sequences set forth in FIG. 1 (SEQ ID NO: 2) or 2 (SEQ ID NO: 4) at the amino acid level. Preferably, the peptide, polypeptide or protein comprise, the N-terminal encoding region of ORF2 which is preferentially interactive with acute phase antibodies to HEV. Alternatively, the peptide, polypeptide or protein comprises the C-terminal encoding region of ORF2 which is preferentially interactive with convalescent phase antibodies to HEV. In a further alternative, the peptide, polypeptide or protein is a full length ORF encoded molecule but chemically or physically modified or disrupted to expose both the N- and C-terminal epitopes.

The present invention also extends to a method for maintaining interactive conformation of synthetic (eg recombinant) peptides or polypeptides wherein the synthetic peptides or polypeptides are further purified after undergoing a denaturation procedure and subsequently renatured. By way of example the synthetic peptide may be denatured by adding denaturing concentrations of buffers including but not limited to, sodium dodecyl sulphate (SDS), 2-mercaptoethanol, or urea. Purification of denatured protein can be undertaken by procedures well known to the skilled artisan including but not limited to procedures for electrophoretic resolution on polyacrylamide gels or size exclusion chromatography. The denaturing buffers are removed by any number of means including but not limited to dilution, dialysis, chromatography or by binding to a solid support, for example membrane support or microtitre plate.

Accordingly, another aspect of the present invention contemplates a method of enhancing the immunointeractivity of a polypeptide or protein encoded by ORF 2 of HEV, said method comprising chemically or physically modifying the polypeptide or protein to enable both convalescent and acute phase antibodies to HEV to bind to said polypeptide or protein without substantial N-terminal inhibition of C-terminal binding to convalescent phase antibodies to HEV.

In a most preferred embodiment, the present invention extends to naturally occurring or synthetic (eg recombinant) peptide, polypeptide or protein corresponding to an approximately 30 KDa protein from the ORF2 region and/or an approximately 14 KDa protein from the ORF3 region and to nucleotide sequences coding for same as well as to fragments, derivatives, homologues or immunological relatives thereof. By "derivatives" is meant to include any single or multiple amino acid substitution, deletion and/or addition relative to the naturally occurring sequence or to the sequences as shown in FIGS. 1 (SEQ ID NO: 2) and 2 (SEQ ID NO: 4) and including any single or multiple substitution, deletion and/or addition to other molecules associated with the peptide or polypeptide including carbohydrate, lipid and/or other proteinacious moieties. Such derivatives, therefore, include glycosylated or non-glycosylated forms or molecules with altered glycosylation patterns.

The present invention is also directed to a method for distinguishing past (i.e. convalescent phase) or contemporary (i.e. acute phase) infection with HEV whether or not by natural infection or following vaccination, whereby the antisera from infected individuals are preferentially immunologically distinguished by interactive peptides of ORF3 or the N-terminus of ORF2. Alternatively, such antisera are preferably immunologically distinguished by interactive peptides of the C-terminal end portion of ORF2.

The present invention also contemplates a method for the detection of antibodies associated with HEV which method comprises contacting a peptide or polypeptide corresponding to all, or an antigenic portion of the epitopic regions of the HEV genome or a derivative thereof with a biological sample from a patient to be tested for a time and under conditions sufficient for a complex to form between the peptide or polypeptide and an antibody reactive to HEV and then detecting the complex. Preferably, the biological sample is serum, a blood derived component such as whole blood, serum or plasma or a secretory component such as saliva. Even more preferably, the peptide or polypeptide is immobilised onto a solid support before, during or after contact with the serum. Methods of detection are well known and include calorimetric, fluorometric and radioactive procedures. Other detection means can also be used such as involving immunoblotting. An example of such immunoblotting techniques includes the well known Western Blot technique. This assay can be varied in any number of ways without departing from the scope of the present invention. Another assay contemplated herein to be useful is the red cell agglutination assay as described by Wilson et al. (1991).

The present invention also extends to the use of peptides or polypeptide corresponding to the epitopic regions of the HEV genome or antigenic fragments thereof, as antigens in a diagnostic test for HEV, or for screening asymptomatic individuals by detection or determination of the titre of antibodies in a patient's serum, for example using enzyme-linked immunoassay or radio immunoassay (RIA) technology or an agglutination assay using antigen-coated beads or the like.

This aspect of the present invention may conveniently be carried out by the detection and/or determination of the titre of antibodies in a biological sample (e.g. whole blood, plasma, serum or saliva) from a human subject, said method comprising contacting said sample with peptides or polypeptides corresponding to epitopic regions of the HEV genome or a fragment or derivative thereof for a time and under conditions sufficient for a complex to form between the peptide or polypeptide and an antibody reactive to HEV and then detecting the complex and/or amount of peptide or polypeptide which has been bound in the complex. Preferably, the peptide or polypeptide is immobilised onto a solid support before, during or after contact with the sample and the peptides or polypeptides are as hereinbefore defined.

Alternatively, HEV infection may be detected or at least a negative result re-confirmed by screening for HEV associated immune complexes. It is possible, for example, that a negative antibody result could have been caused by antibodies forming complexes with HEV thereby not being available for binding in the aforementioned assay. To conveniently detect HEV immune complexes, serum or other biological fluid is contacted with an anti-HEV antibody (e.g. a monoclonal antibody) for a time and under conditions sufficient for a HEV-antibody immune complex to bind. Preferably, the anti-HEV antibody is first immobilised onto a solid support. An anti-immunoglobulin antibody, generally with a label or other reporter molecule attached, is then used to screen for the antibody component of the HEV complex.

One skilled in the art will immediately recognise that the assays as contemplated herein may be modified without departing from the scope of the present invention. All such modifications and variations of these assays are encompassed by the present invention.

The presence of HEV convalescent and/or acute phase antibodies in a subject's biological fluid (such as whole blood, plasma, serum or saliva) can be detected using a wide range of immunoassay techniques such as those described in U.S. Pat. Nos. 4,016,043, 4,424,279 and 4,018,653. This includes both single-site and two-site, or "sandwich", assays of the non-competitive types, as well as in the traditional competitive binding assays. Sandwich assays are particularly useful and include ELISA dip-stick assays and Immunofluorometric assays (IFA). Competitive binding assays include radioimmunoassays (RIA). Western blot assays may also be used. The choice of assay will depend on the sensitivity required, materials available and the biological sample employed.

A number of variations of the sandwich assay technique exist, and all are intended to be encompassed by the present invention. Briefly, in one assay, an unlabelled peptide, polypeptide or protein (hereinafter abbreviated to "polypeptide") capable of preferably binding to acute or convalescent phase antibodies to HEV is immobilised onto a solid substrate and the biological sample to be tested for HEV antibodies brought into contact with the bound molecule. After a suitable period of incubation, for a period of time sufficient to allow formation of a polypeptide-antibody primary complex, an immunoglobulin specific antibody, labelled with a reporter molecule capable of producing a detectable signal, is then added and incubated, allowing time sufficient for the formation of a secondary complex of polypeptide-antibody-labelled antibody. Any unreacted material is washed away, and the presence of the VPF is determined by observation of a signal produced by the reporter molecule on the second antibody. The results may either be qualitative, by simple observation of the visible signal or may be quantitated by comparing with a control sample containing known amounts of HEV antibody. Variations of this assay include a simultaneous assay, in which both sample and labelled antibody are added simultaneously to the bound polypeptide, or a reverse assay in which the labelled antibody and sample to be tested are first combined, incubated and then added simultaneously to the bound polypeptide. These techniques are well known to those skilled in the art, and the possibility of variations will be readily apparent. The antibodies used above may be monoclonal or polyclonal.

In this assay, the HEV derived polypeptide or antigenic parts thereof is either covalently or passively bound to a solid surface. The solid substrate is typically glass or a polymer, the most commonly used polymers being cellulose, polyacrylamide, nylon, polystyrene, polyvinyl chloride or polypropylene. The solid supports may be in the form of tubes, beads, discs or microtitre plates, or any other surface suitable for conducting an immunoassay such as a dipstick. The binding processes are well-known in the art and generally consist of cross-linking, covalently binding or physically adsorbing the molecule to the insoluble carrier.

By "reporter molecule", as used in the present specification, is meant a molecule which, by its chemical nature, produces an analytically identifiable signal which allows the detection of an HEV polypeptide-antibody complex. The most commonly used reporter molecules in this type of assay include enzymes, fluorophores and radionuclide containing molecules (i.e. radioisotopes). In the case of an enzyme immunoassay, an enzyme is conjugated to the antimmunoglobulin antibody, generally by means of glutaraldehyde or periodate. As will be readily recognised, however, a wide variety of different conjugation techniques exist which are readily available to one skilled in the art. Commonly used enzymes include horseradish peroxidase, glucose oxidase, β-galactosidase and alkaline phosphatase, amongst others. The substrates to be used with the specific enzymes are generally chosen for the production, upon hydrolysis by the corresponding enzyme, of a detectable colour change.

Alternatively, fluorescent compounds, such as fluorescein, anthanide such as europium and rhodamine, may be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. As in an enzyme immunoassay (EIA), the fluorescent labelled antibody is allowed to bind to the polypeptide in the polypeptide-antibody complex. After washing off the unbound reagent the remaining complex is then exposed to the light of the appropriate wavelength, the fluorescence observed indicates the presence of the hapten of interest.

Immunofluorescence and EIA techniques are both very well established in the art and are particularly preferred for the present method. However, other reporter molecules, such as radioisotopes, chemiluminescent molecules or bioluminescent molecules may also be employed. It will be readily apparent to the skilled technician how to vary the procedure to suit the required purpose.

Accordingly, one aspect of the present invention contemplates a method of detecting convalescent and/or acute phase antibodies in HEV in a biological sample, said method comprising the steps of contacting said biological sample with an immobilised polypeptide preferably interactive with acute phase or convalescent phase antibodies to HEV for a time and under conditions sufficient for a polypeptide-antibody complex to form and subjecting said complex to a detecting means. The latter complex may be detected by, for example, the addition of an antimmunoglobulin antibody labelled with a reporter molecule.

Alternatively, a competitive immunoassay may be used. The most convenient assay of this type is a radioimmunoassay (RIA). In another assay, the red cell agglutination test may be employed (see Wilson et al. 1991).

The invention also extends to use of the peptides and/or polypeptides, or fragments, or derivatives of the present invention in the treatment or prophylaxis of patients.

As contemplated herein prophylaxis may be achieved in a patient by immunising a patient with a vaccine containing antigens corresponding to the epitopic regions of the HEV genome and a suitable adjuvant sufficient to elicit an antibody response in a patient. Methods for production of vaccines are well known to those skilled in the art and by way of example a convenient reference is Remington's Pharmaceutical Sciences, 17th ed., Mack Publishing Co., Easton, Pa., USA. Preferred HEV antigens include the N-terminal region of ORF2 or the C-terminal region of ORF2.

Due to the nature of the epitopic region(s) of the HEV antigen it should therefore be possible to discriminate between naturally infected individuals and vaccinated individuals.

The present invention encompasses other forms of kits and diagnostic assays including a kit comprising a container adapted to contain a synthetic peptide or polypeptide corresponding to the epitopic region of the HEV genome or its fragments, derivatives, homologues and/or immunological relatives. Preferred antigens are the N-terminal region of ORF2 and the C-terminal region of ORF2 of HEV. The kit may contain a second container adapted to contain or receive a sample to be tested. A third container may be present adapted to contain reagents for detecting HEV-antibody complexes. Alternatively, where the kit is to detect HEV immune complexes, the kit may comprise one or more containers (e.g. wells) adapted to contain a HEV specific antibody (e.g. a monoclonal antibody). Additional containers with the kit may then contain receptacles for receiving fluid samples and a labelled antibody.

In further accordance with the present invention, expression of the cDNA insert encoding the epitopic regions of HEV described herein or fragments thereof, may be achieved in a number of different ways.

As an example, successful expression of the antigens encoding the epitopic regions of HEV as a fusion protein can be achieved using the pGEX vectors which give expression of glutathione S-transferase fusion proteins, using *E. coli* as the host cells. Expression could also be achieved, by way of example, using pEV vectors or the polyhistidine expression vectors again using *E. coli* as the host cells. Any other suitable fusion protein capable of use in a bioaffinity chromatography may also be employed such as polylysine, FLAG and thioredoxin. Alternatively, the epitopic region of HEV may be expressed as a non-fused polypeptide, by using appropriate vector and host cell combinations. Other vector and host cell combinations which can be used in accordance with the present invention including a number of well described yeast shuttle vectors for use in yeast cells, or eukaryotic vectors useful in continuous cell lines, (eg CHO cells) yeast cells and/or insect cells or transgenic animals.

The present invention is applicable to any strain of HEV which has a genomic organisation comprising open reading frames equivalent to ORF2 and ORF3 as defined by Tam et al (1991). Of the strains isolated to date, any strain of HEV is useful in the practice of the present invention.

The present invention will now be further described with reference to the following non-limiting Figures and Examples.

In the Figures:

Figure 2:
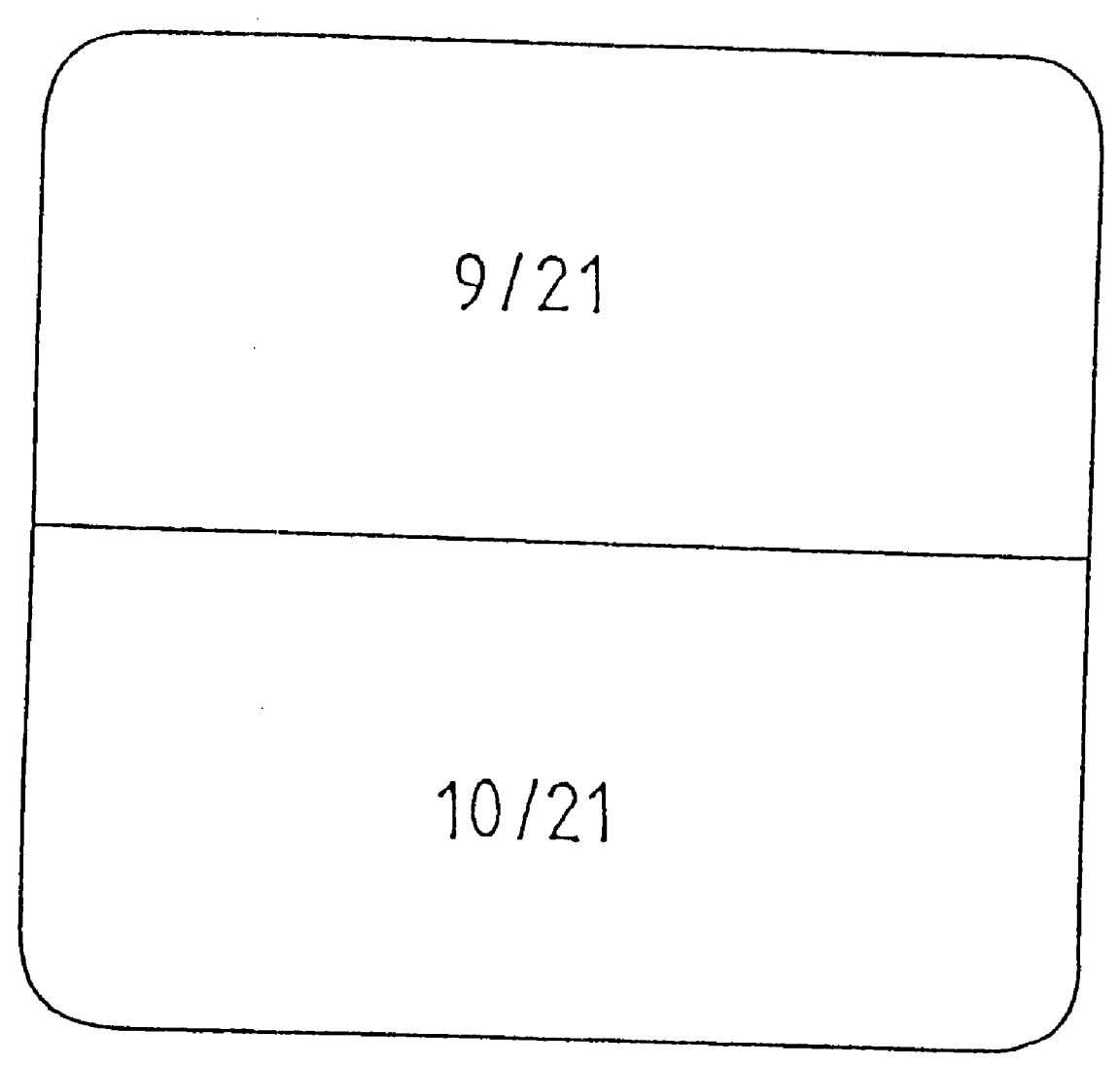

FIG. 2 shows the nucleotide deduced amino acid sequences of the 14 kDa protein encoded by Open Reading Frame 3 of the HEV genome, of the strain of hepatitis E virus isolated from an epidemic in Xinjiang autonomous region of China.

FIG. 4 shows a comparison of the results obtained using the Western blot of the present invention to screen sera samples from an Australian Aboriginal population versus results obtained with a commercially available EIA for HEV (Genelabs Diagnostics, Singapore).

Figure 5:
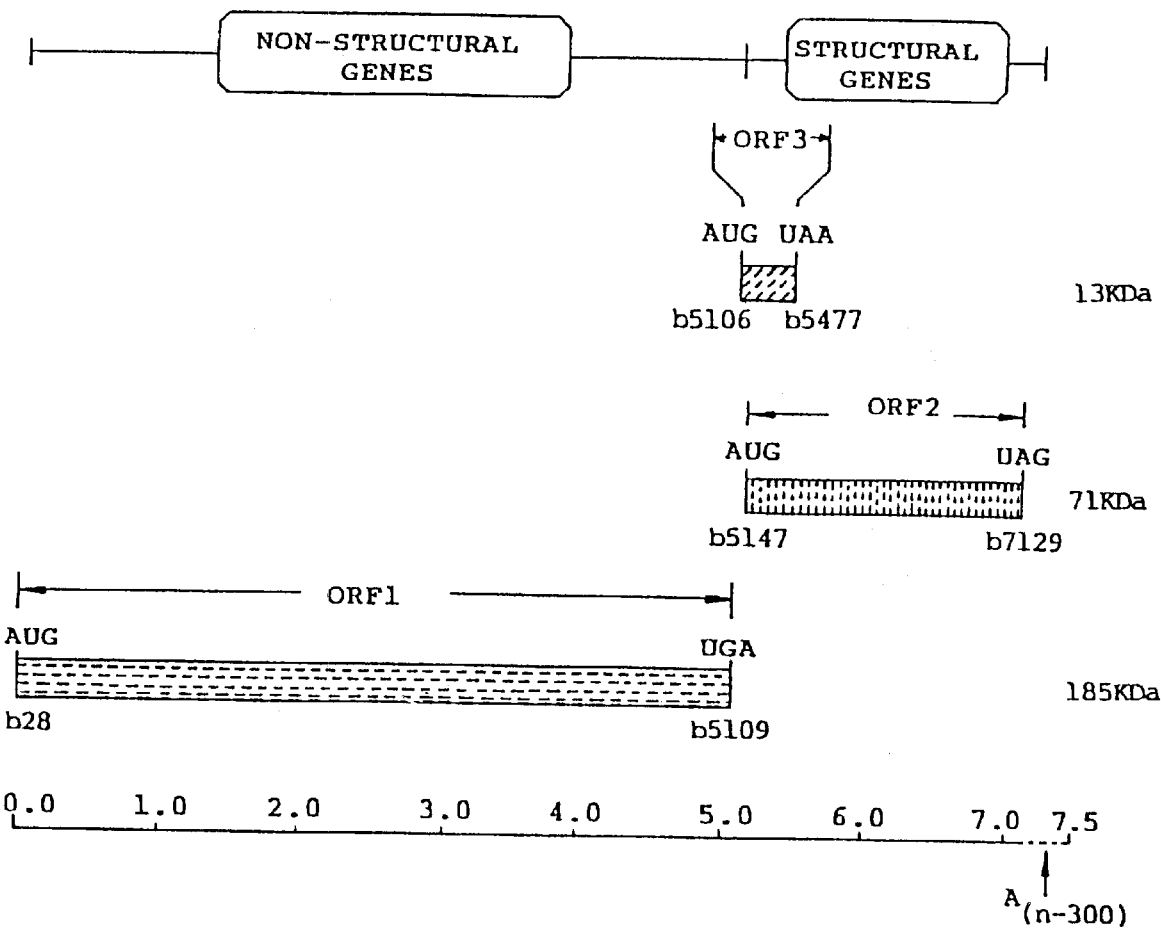
Figure 5:
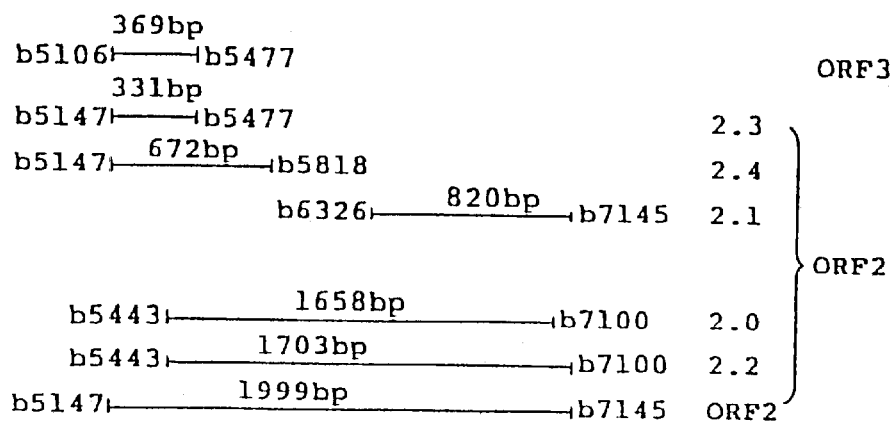

FIG. 5 shows the cloning strategy for the recombinant HEV-GST fusion proteins herein described. The cDNA fragments of 1658, 830 and 380 bp were generated after reverse transcription and PCR of HEV RNA extracted from the bile of an experimentally infected monkey. All DNA fragments were purified by agarose gel electrophoresis and Prep-A-Gene at each step.

Figure 6A:
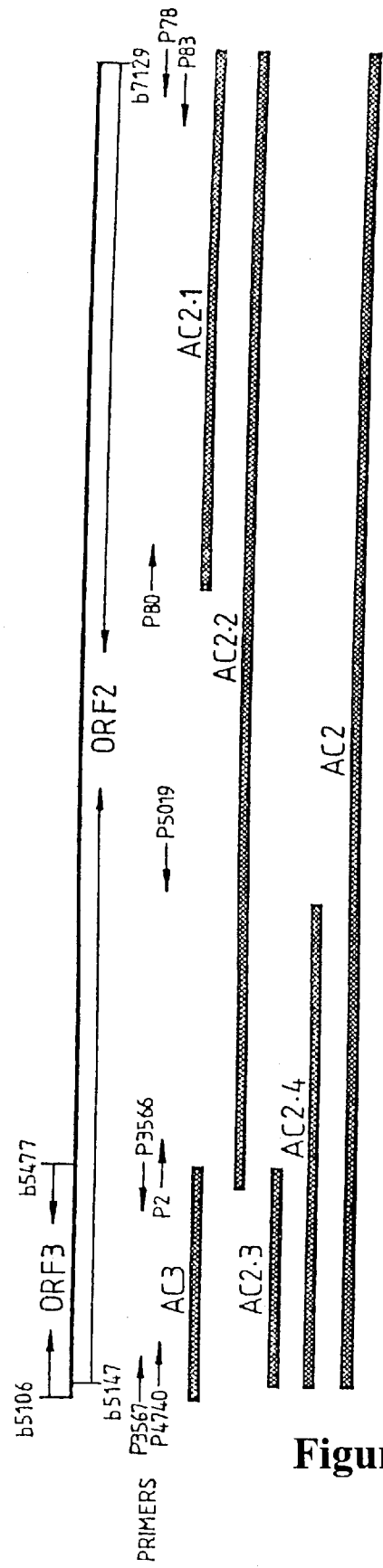
Figure 6B:
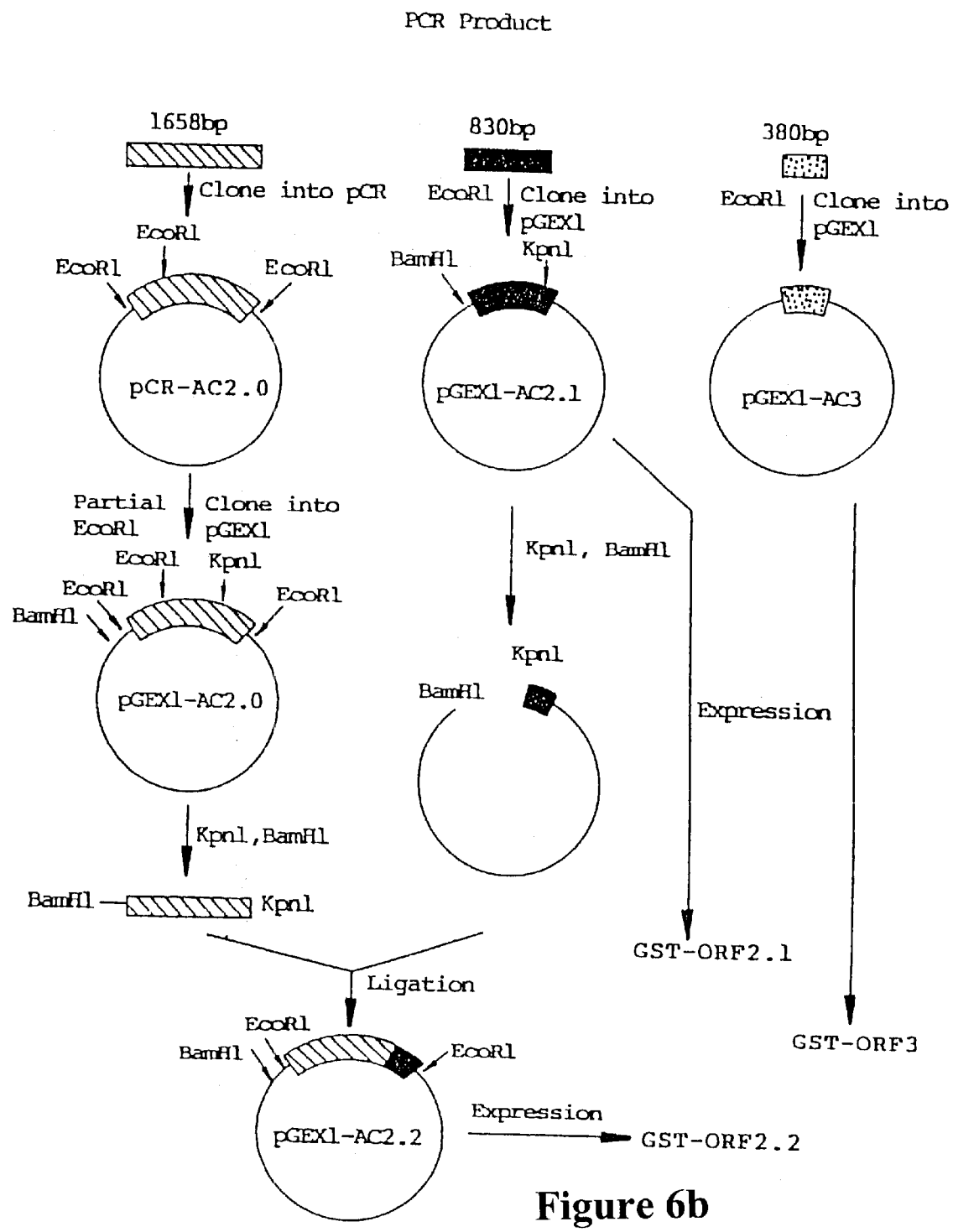
Figure 6C:
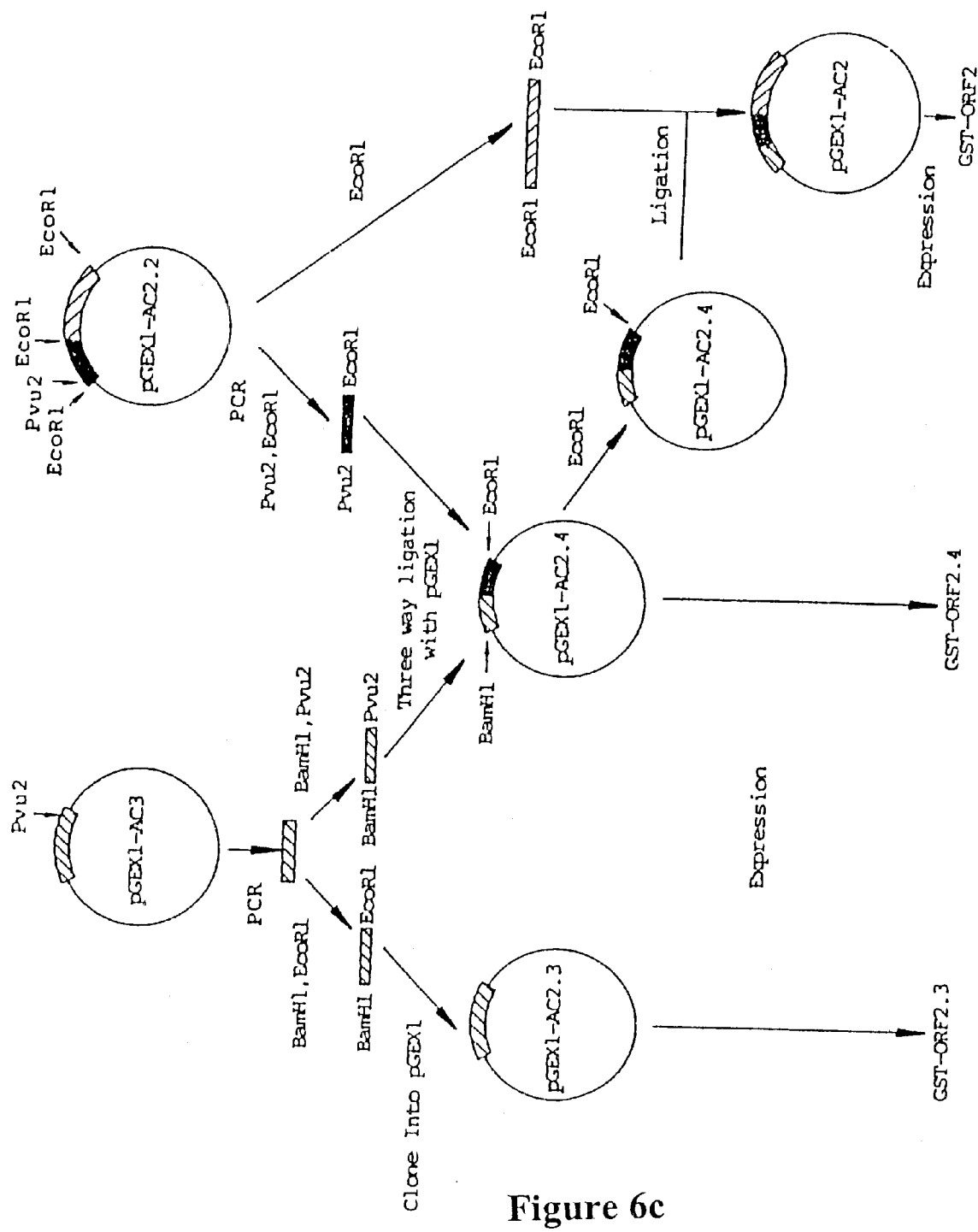

FIG. 6 shows the cloning strategies for (FIG. 6A): HEV cDNA clones; (FIG. 6B): recombinant HEV-GST fusion proteins ORF3, ORF2.1 and ORF2.2; and (FIG. 6C): the recombinant HEV-GST fusion proteins ORF2, ORF2.3 and ORF2.4. The recombinant HEV-GST fusion proteins herein described. The cDNA fragments of 1658, 830 and 380 bp were generated after reverse transcription and PCR of HEV RNA extracted from the bile of an experimentally infected monkey, while other PCR products were generated from the clones pGEX1-AC3 and pGEX1-AC2.2. All DNA fragments were purified by agarose gel electrophoresis and Prep-A-Gene at each step.

Figure 1:
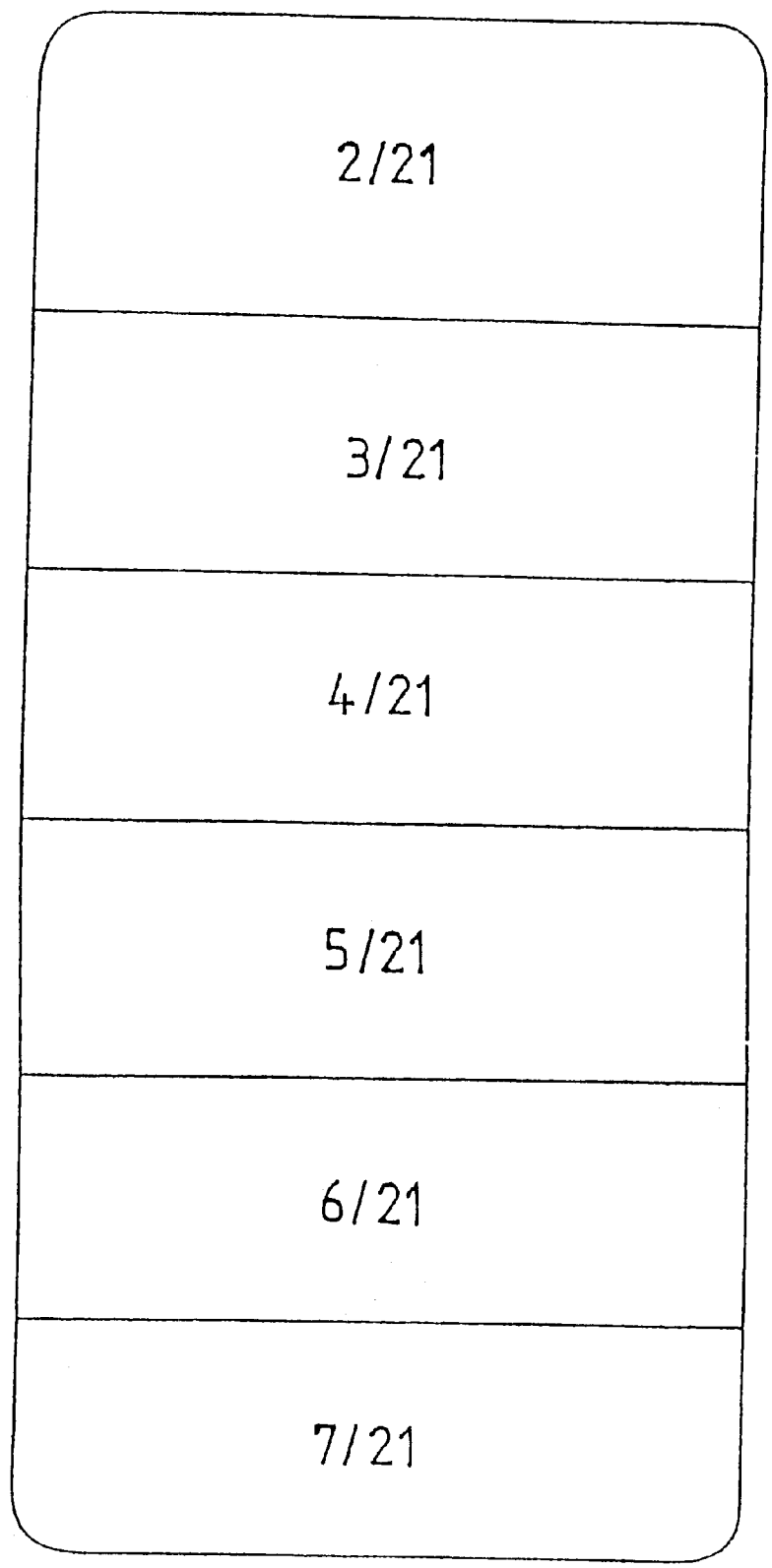
FIG. 1 shows the nucleotide and deduced amino acid sequence of the 76 kDa protein encoded by Open Reading Frame 2, of the strain of hepatitis E virus isolated from an epidemic in Xinjiang autonomous region of China.
Figure 3:
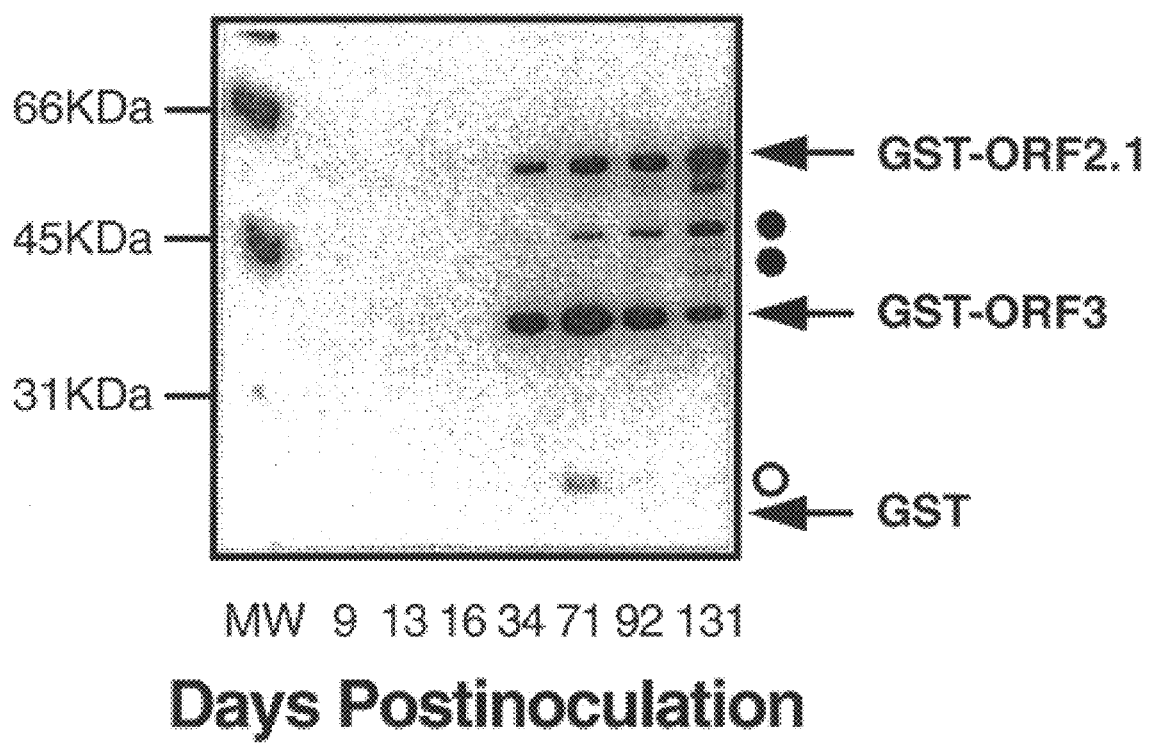
FIG. 3 shows a Western blot of sera taken at differing time points from an infection of a rhesus monkey (Macaca mulatta) with the HEV virus using the 56 kDa and/or 39 kDa fusions proteins or GST as antigen.
Figure 7:
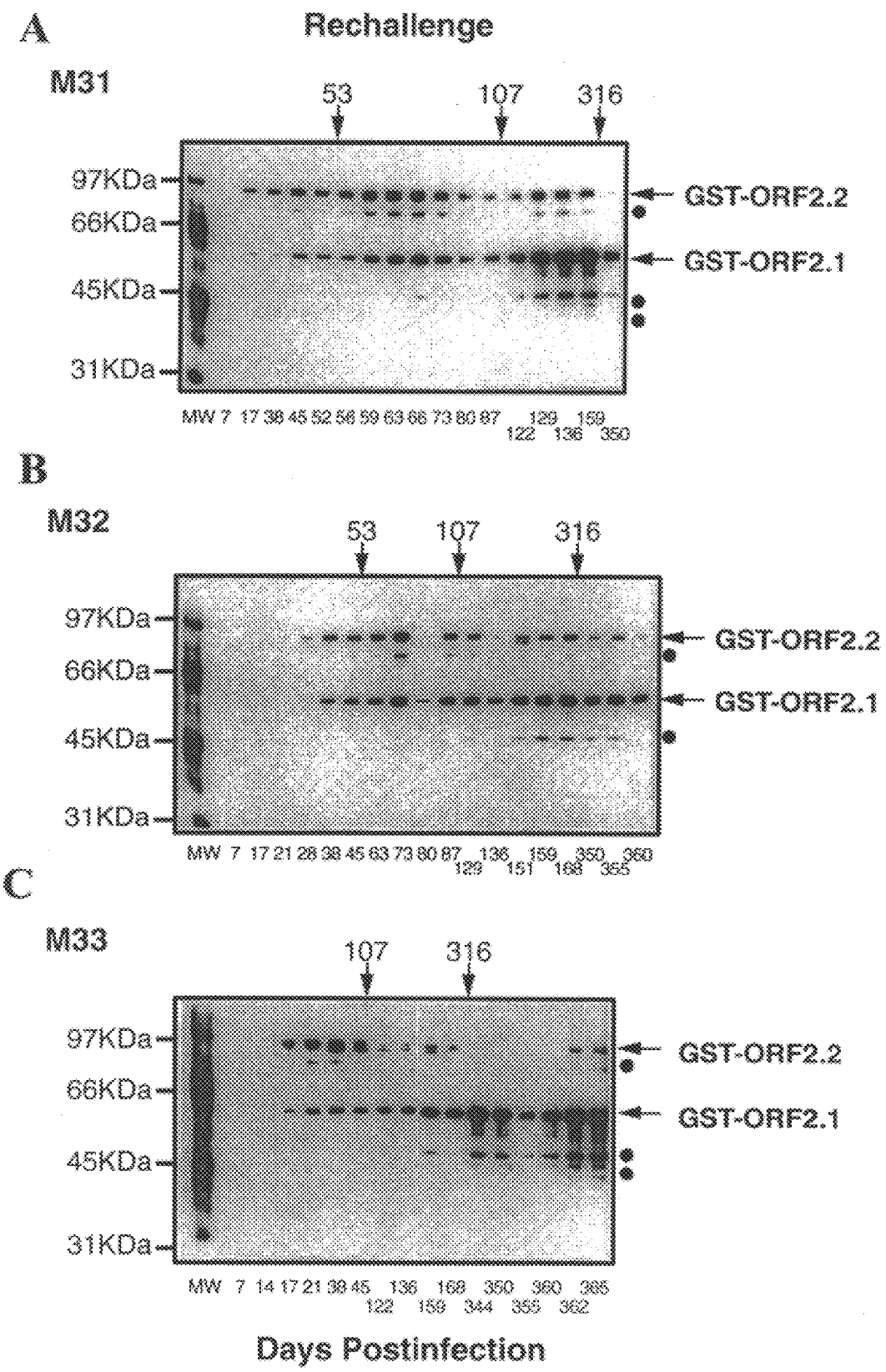

FIG. 7 is a Western blot of GST-ORF2.1 and GST-ORF2.2 with sera from infected macaques. GST and fusion proteins GST-ORF2.1 and GST-ORF2.2 were mixed in equal proportions, electrophoresed and transferred essentially as in FIG. 3. (FIG. 7A), (FIG. 7B), (FIG. 7C) monkeys M31, M32 and M33, respectively. Lane MW, biotinylated molecular weight markers (sizes indicated at left) Note that reactivity to GST-ORF2.1 is weaker than that to GST-ORF2.2 during the acute phase of infection, but is boosted after rechallenge and subsequently remains at higher levels than that to GST-ORF2.2.

Figure 8A:
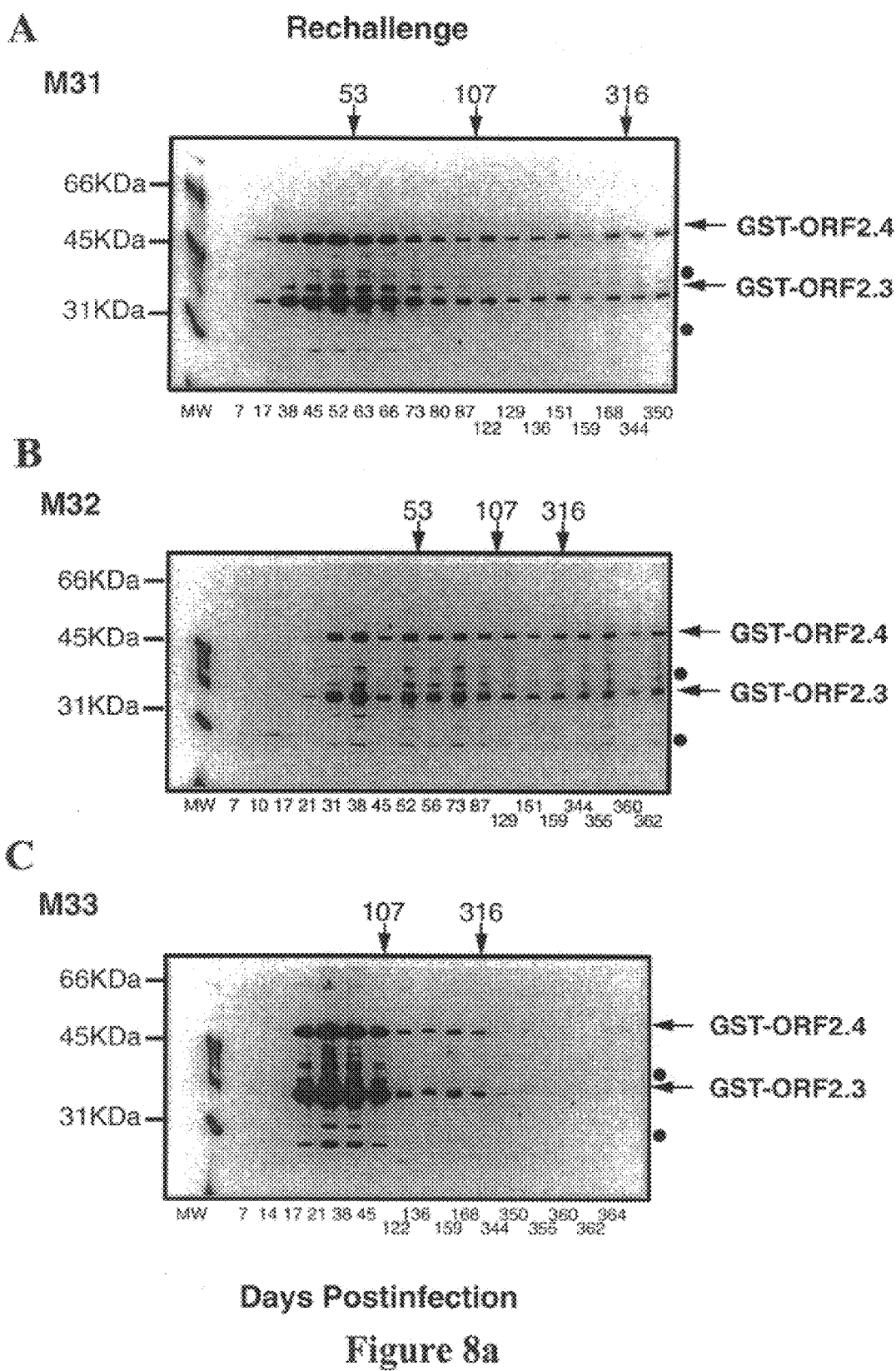
Figure 8B:
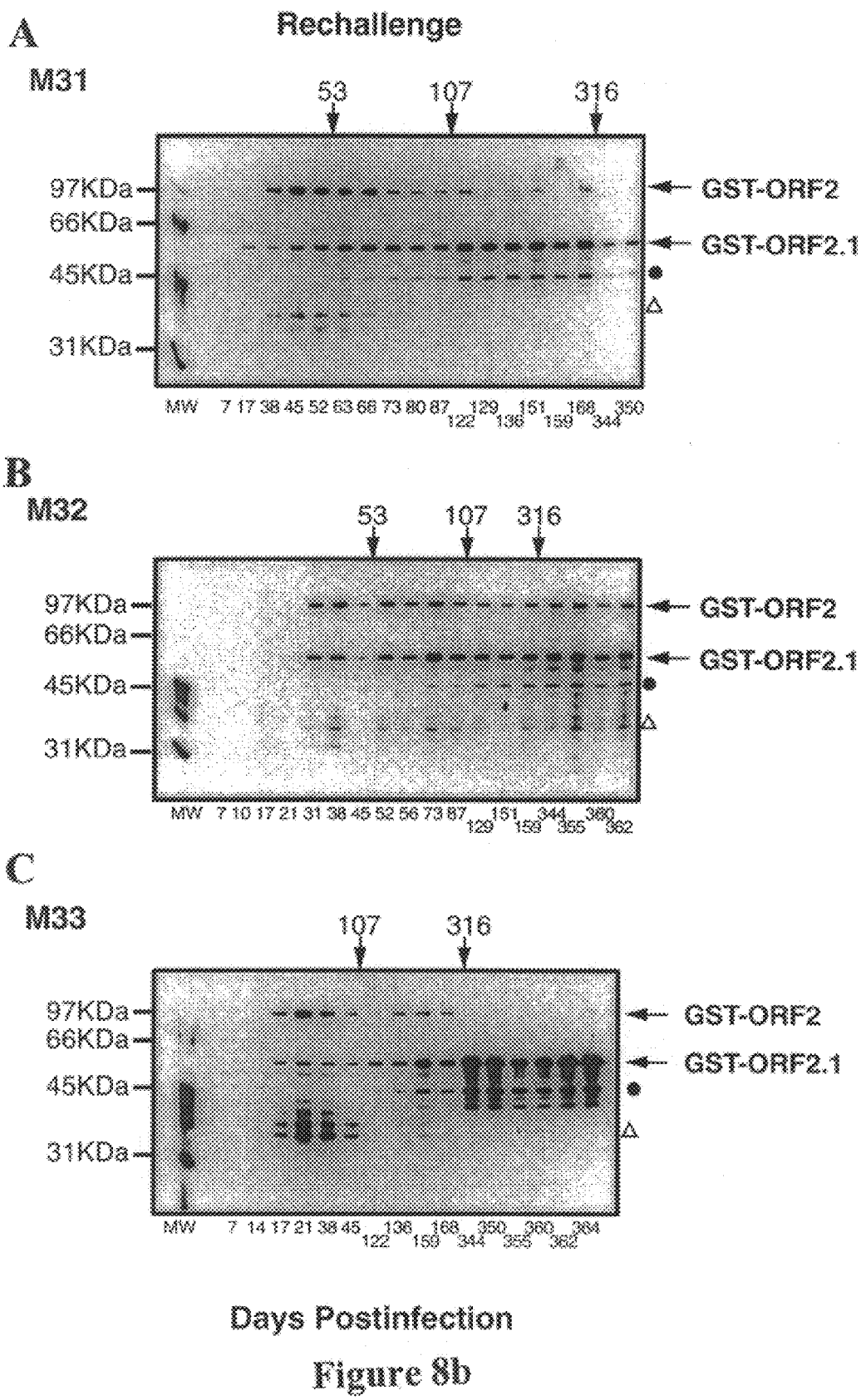

FIGS. 8A and 8B are Western blots of (8A) GST-ORF2, GST-ORF2.1, (8B) GST-ORF2.3 and GST-ORF2.4, with sera from infected macaques. GST and fusion proteins were mixed in equal proportions, electrophoresed and transferred essentially as in FIG. 3. In each panel, (A), (B), (C), monkeys M31, M32, and M33. Lane MW, biotinylated molecular weight markers. Note that the reactivity of GST-ORF2 appears to lie in the N-terminal sequences overlapping with GST-ORF2.3 and GST-ORF2.4: breakdown products of GST-ORF2 as well as the shorter GST-ORF2.3 and GST-ORF2.4 fusion proteins are strongly reactive with acute phase sera.

Figure 9:
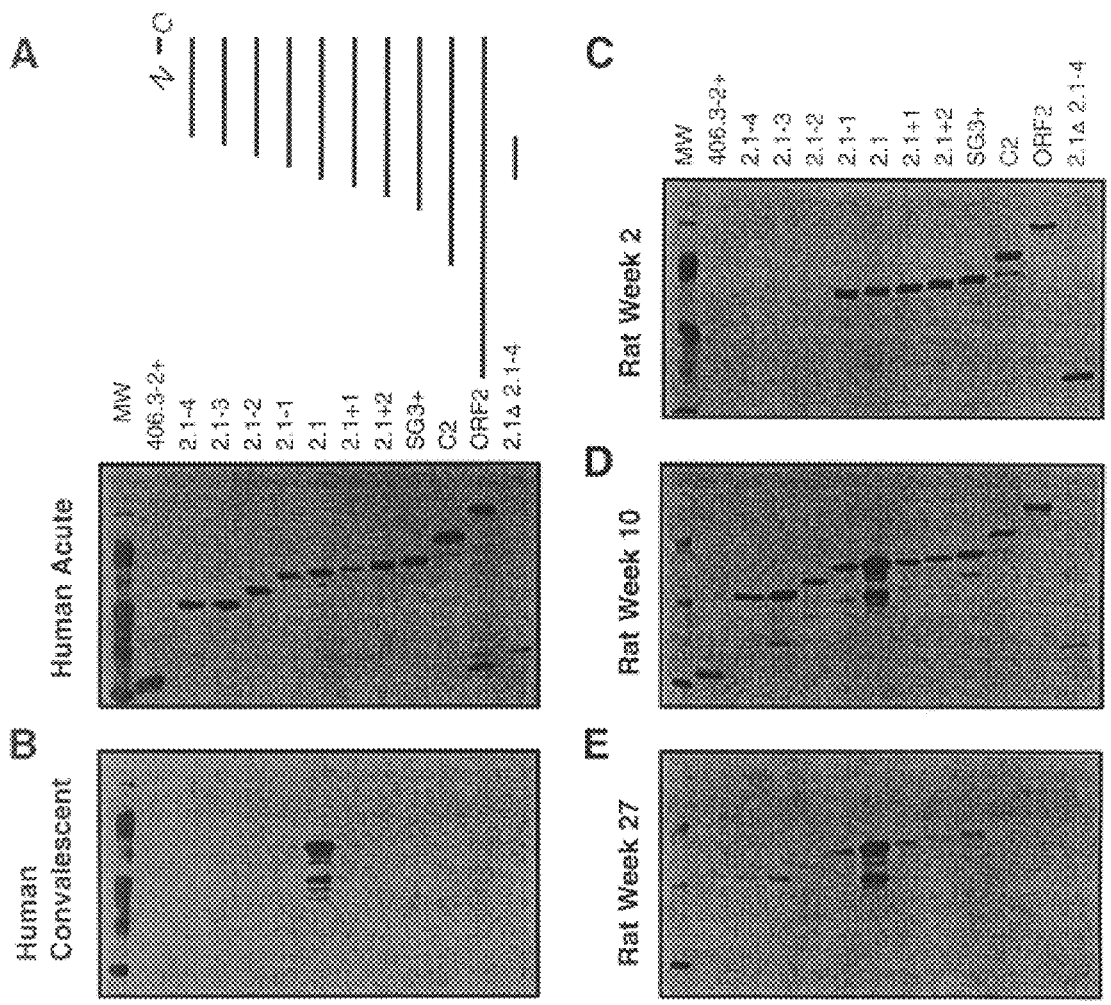

FIG. 9 shows western immunoblotting to detect antibody to HEV. A schematic representation of the ORF2 proteins is shown above the figure. Recombinant proteins containing GST fused to the N-terminus of different fragments of ORF2 (as shown) were loaded on SDS-PAGE gels, and after electrophoresis were transferred to nitrocellulose membranes. The amount of each protein loaded was adjusted such that immunoblotting with antibody to GST gave equivalent staining of each lane, represent equimolar amounts of protein on the membrane.

(FIG. 9A) Human acute-phase sera reacts with all ORF2 constructs to an equal extent. (FIG. 9B) Human convalescent-phase sera reacts only with ORF2.1. (FIG. 9C) Rats immunized with purified ORF2.1 absorbed to Alum develop a response against diverse epitopes present in most constructs of ORF2 by 2 weeks after primary immunization. (FIG. 9D) At 10 weeks after primary immunization, with boosting at 4 weeks, antibody is against ORF2.1. (FIG. 9E) At 27 weeks after primary immunization, with boosting at 4 weeks and 12 weeks, antibody is against ORF2.1.

Figure 10:
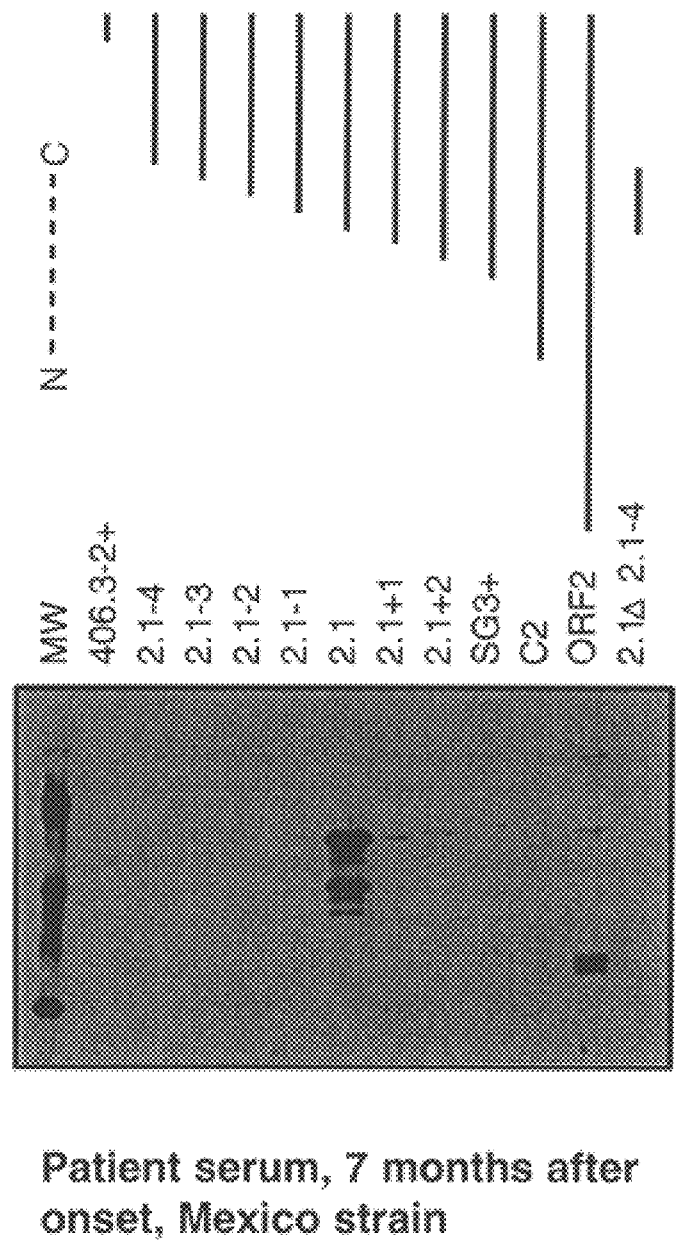

FIG. 10 shows that the ORF2.1 epitope is highly conserved between divergent HEV strains. Convalescent (7 months) serum from a patient infected with the Mexico strain of HEV reacts with the ORF2.1 epitope. In addition, reactivity is seen against a breakdown product of full-length ORF2, which is analogous to the ORF2.3 fragment.

Figure 11:
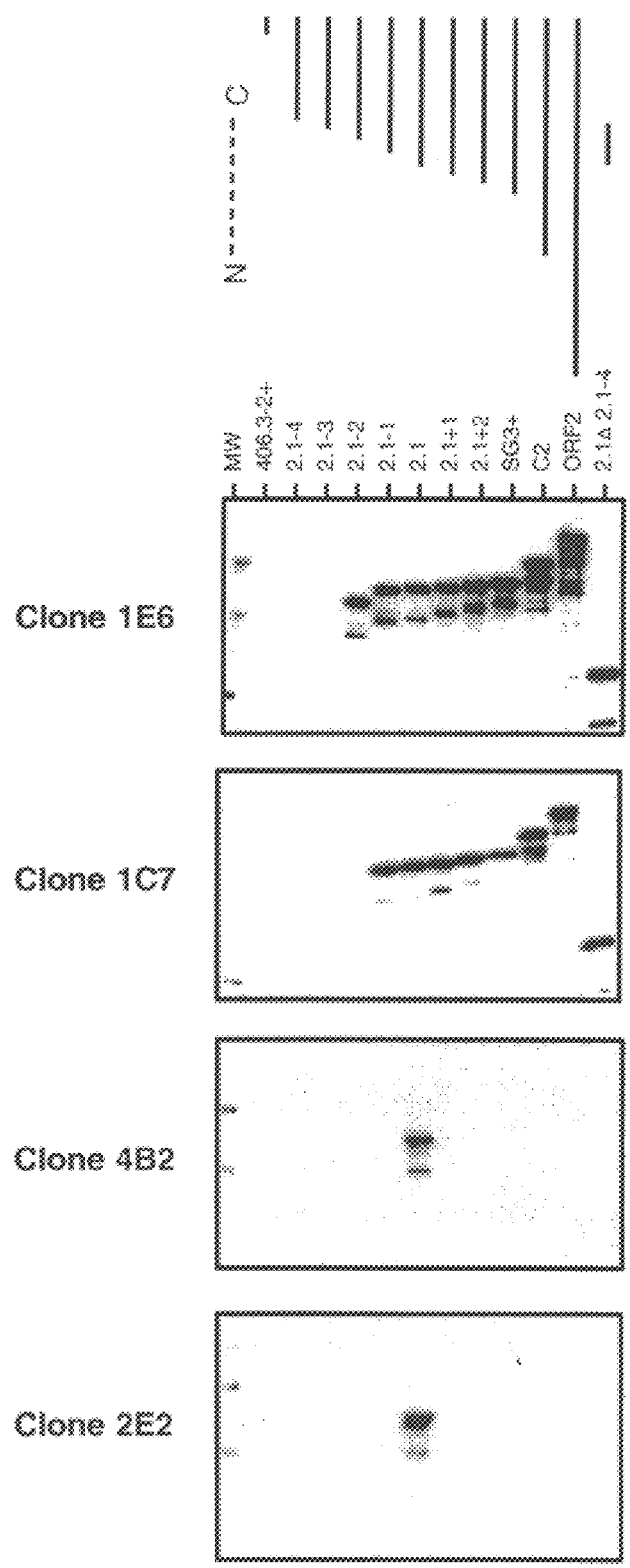

FIG. 11 shows specificity of monoclonal antibodies induced by immunization with ORF2.1. Of four independent antibody-producing lines, clones 1E6 and 1C7 react against linear epitopes present in all constructs larger than 2.1-2 and 2.1-1, respectively, whereas clones 4B2 and 2E2 react against the conformational ORF2.1 epitope (western blot as in FIG. 9).

Figure 12:
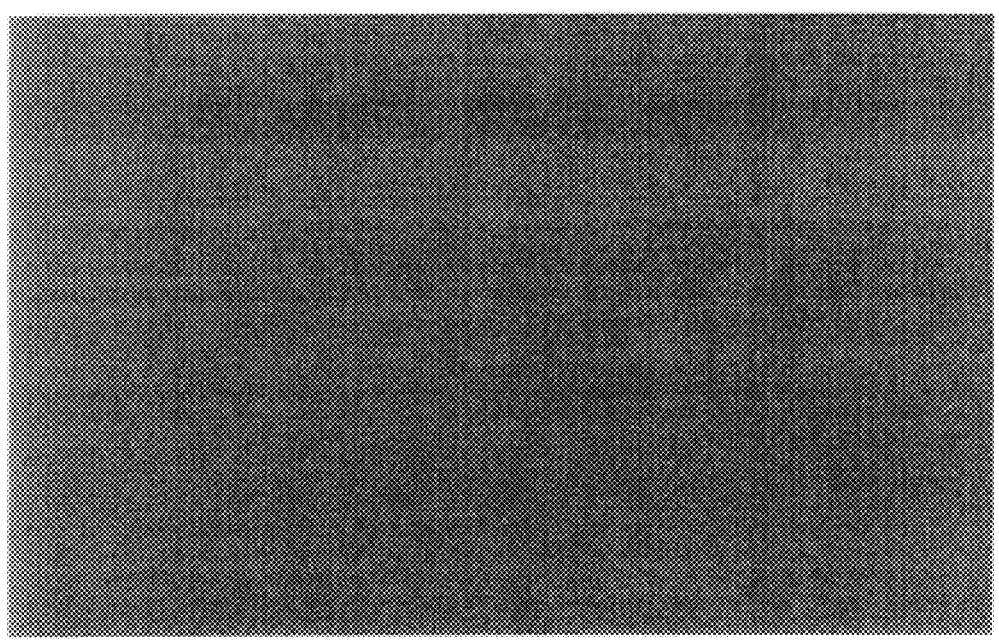
Figure 12:
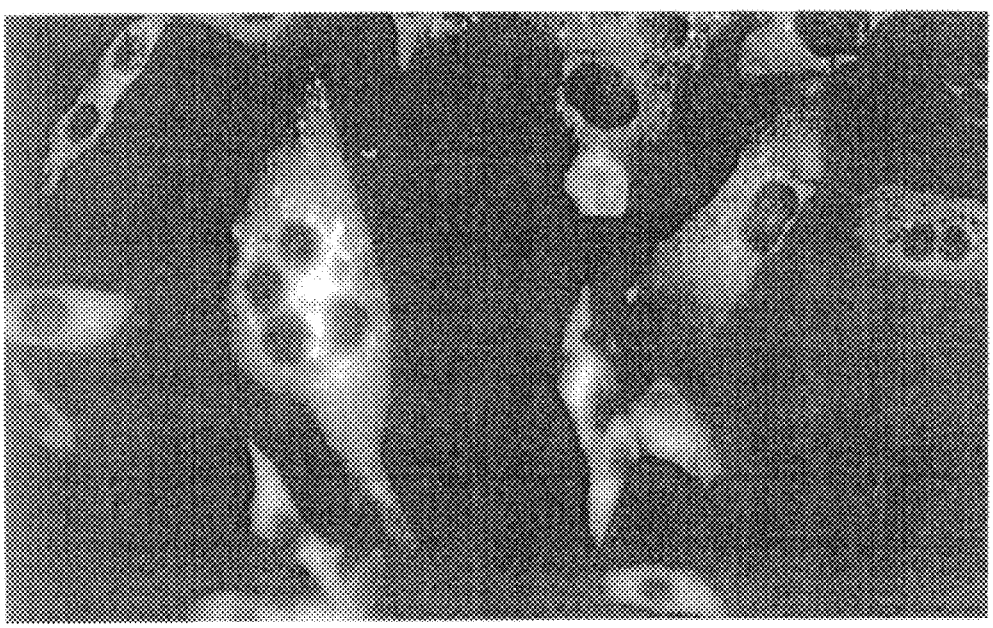

FIG. 12 shows that the conformational ORF2.1 epitope is present in full-length ORF2 expressed in mammalian cells, and is therefore a "native" epitope of the virus. BHK cells were mock-infected (FIG. 12A) or infected with recombinant SFV-HEV ORF2 particles (FIG. 12B) and fixed at 18 hours postinfection for staining with monoclonal antibody 4B2 (specific for the conformational ORF2.1 epitope, FIG. 11)

EXAMPLE 1

Hepatitis E Virus and Antigens Therefrom

The strain of HEV used in these studies was isolated from infected individuals from the Xinjiang autonomous region of China during an epidemic between September 1986 and April 1988.

Aye TT et al (1992) reported that an HEV strain isolated from infected individuals from the Xinjiang autonomous region of China had 93.9% nucleotide sequence homology with the Burmese strain (Tam et al., 1989).

Virus was cultured by infecting rhesus monkeys with fecal samples from infected individuals, using known methods (Cao, X-Y et al, 1991). The monkeys were acutely infected, with the HEV being excreted into the bile and faeces of the monkey.

The viral antigens were isolated as follows using reverse transcriptase PCR.:
(a) Extraction of RNA from bile. Bile specimens were collected directly from the gall bladder of an infected rhesus monkey at day 7–14 after inoculation. An aliquot of 10 μl of bile was mixed with 25 μl nuclease free water and 465 μl GIT (4M guanidine thiocyanate, 25 mM sodium citrate, 0.5% v/v sarkosyl, 0.1M 2-mercaptoethanol). An aliquot of 50 μl of 3M sodium acetate (pH5.2) was added to the mixture above followed by extraction with 450 μl phenol/chloroform (5:1). After separation by centrifugation, the upper phase was transferred to a fresh tube containing 2 μl of 10 mg/ml tRNA. The RNA was precipitated in 750 μl of ice-cold isopropanol at −20° C. for a minimum of 2 hours, then pelleted at 13,000 rpm for 15 minutes, washed with 80% v/v ethanol and repelleted as above. The dried pellet was resuspended in 10 μl of nuclease free water and incubated at 65° C. for 10 minutes, then stored at 4° C. ready for RT-PCR. A similar method may be used on faeces.
(b) Primers. Two pairs of primers were designed to isolate the whole fragment of ORF3 and one third of the 3' end of ORF2 (ORF2.1), respectively. These primers were modified to contain EcoR1 restriction sites to facilitate cloning. The nucleotide sequences of the primers, with the HEV-specific sequences underlined, are:

For ORF3: 5'-GTGAATTC ATGAATAACATGTCTTTTGC-3'(forward)(SEQ ID NO: 5)
5'-GTGAATTC TTAGCGGCGCGGCCCCAGCT-3'(reverse)(SEQ ID NO: 6)
For ORF2: 5'-GTGAATTC CAGCTGTTCTACTCCCGTCC-3'(forward)(SEQ ID NO: 7)
5'-GTGAATTC GGCACTTCGTTTATTTGATGTT-3'(reverse)(SEQ ID NO: 8)

A third primer pair was designed to amplify approximately two thirds of ORF2, terminating 27 nucleotides from the carboxy terminus (ORF2.0) This PCR product did not contain modified restriction enzyme sites, and instead was cloned using the 3' A overhang.

ORF2.0: 5'-TCGTAGACCTACCACAGCTG-3'(forward)(SEQ ID NO: 9)
5'-TCTTAAGGCGCTGAAGCTCA-3'(reverse)(SEQ ID NO: 10)

These primer sets were designed on the basis of published sequences for HEV.

To extend the collection of cDNA clones (FIG. 6C), the first primer pair was designed to amplify the amino-terminal 330 bp of ORF2 (ORF2.3). These primers were modified to contain BamH or EcoR1 restriction sites to facilitate cloning. The nucleotide sequences of primers, with the HEV-specific sequences underlined, are:

P4740: 5'-GTGGATCC ATGCGCCCTCGGCCTATTTTGT-3'(forward)(SEQ ID NO: 11)
P3566: 5'-GTGAATTC TTAGCGGCGCGGCCCCAGCT-3'(reverse)(SEQ ID NO: 12)

The second primer pair was designed to amplify 440 bp fragment of ORF2 which overlaps AC2.3.

P2: 5'-TCGTAGACCTACCACAGCTG-3'(forward) (SEQ ID NO: 13)
P5019: 5'-CACAAGCTCAGAGGCTATGCCG-3' (reverse)(SEQ ID NO: 14)

(c) RT-PCR. Prior to PCR amplification, the RNA was reverse transcribed into cDNA. To each RNA sample, 10 μl of RT Master Mixture (41 μl 25 mM MgCl$_2$, 2.0 μl 10XRT buffer, 2.0 μl 10 mM dNTP mixture, 0.1 μl 200 ng/μl reverse primer, 0.5 μl rRNAsin, 0.5 μl AWV RT) was added. After a 60 minute incubation at 42° C., the reaction was boiled for 5 minutes and quenched in chip ice for 5 minutes. For the PCR reaction, 30 μl of PCR Master Mixture (19.1 μl nuclease free water, 3.6 μl 25 mM MgCl$_2$ 3.0 μl 10XTaq Buffer (500 mM KCl, 100 mM Tris pH 9.0, 1% v/v Triton X-100), 3.0 μl 2 mM dNTP, 1.0 μl forward primer, 0.3 μl AmpliTaq DNA polymerase (Promega) was mixed with the cDNA reaction and overlayed with 50 μl mineral oil. The amplifications were carried out in a thermocycler (DNA Thermal Cycler 480, PERKIN ELMER CETUS) with the following cycling program: 94° C. denaturaton for 1 minute, 55° C. annealing from 1 minute and 72° C. extension from 2 minutes. A total of 40 cycles were processed followed by a final extension at 72° C. for 7 minutes.

EXAMPLE 2

Construction of Expression Vectors

The plasmids and cloning strategy used in this study are shown in FIGS. 5 and 6. PCR products were separated on a 1.0% v/v agarose gel. Fragments of about 380 bp (ORF3), 830 bp (ORF2.1) and 1658 bp (ORF2.0) were recovered by cutting the bands out of the gel. The DNA was purified using the Pre-A-Gene kit (Bio-Rad, USA). Fragments ORF3 and ORF2.0 were digested with EcoR1 and the restriction fragments (370 bp or 820 bp) were separated on a gel and purified as above. Approximately 6 ng of ORF3 or 16 ng of the ORF 2.1 DNA were ligated with 10 ng of pGEXI vector EcoR1 cut, dephosphorylated, (Pharmacia Biotech, USA) to give the plasmids pGEX1-AC3 and pGEX1-AC2.1, respectively, transformed into E. coli strain NM522 (Pharmacia Biotech, USA) using the Gene Pulser (Bio-Rad, USA), and plated on LB-ampicillin. Plasmids were prepared from transformants by minipreparation and following EcoR1 digestion were examined for inserts of the expected sizes. Fragment ORF2.0 (20 ng) was ligated with 50 ng of dephosphorylated vector pCR (Invitrogen, San Diego, Calif.) utilizing the T overhangs on plasmid and A overhangs on PCR product to give the plasmid pCR-AC2.0. After transformation and selection of recombinants, purified plasmids were subjected to partial EcoR1 digestion and the resulting fragment of 1670 bp purified and ligated into pGEX1 as above to give plasmid pGEX1-AC2.0. This plasmid and pGEX1-AC2.1 were digested to completion with Kpn1 and BamH1. The restriction fragment of 1390 bp from pGEX1-AC2.0 was then ligated with the fragment from pGEX1-AC2.0 containing the pGEX 1 sequence together with the ORF2 sequences downstream of the Kpn1 site, to generate plasmid pGEX1-AC2.2.

The plasmids and cloning strategy used in this study are shown in FIGS. 5 and 6. Three clones, pGEX1-AC3, pGEX1-AC2.1 and pGEX1-AC2.2, were constructed in this laboratory earlier. DNA from plasmid pGEX1-AC3 and pGEX1-AC2.2 were extracted by minipreparation and used as templates for PCR to amplify two overlaped fragments. A PCR product from pGEX1-AC3 (ORF2.3), which contains 330 bp nucleotides of 5' end of ORF2, was digested with BanH1 and EcoR1 and ligated with pGEX1, to generate plasmid pGEX1-AC2.3. Another PCR product from pGEX1-AC2.2 was digested with Pvu 2 and EcoR1 (360 bp) and ligated with the restriction fragment of 312 bp from ORF2.3 after BamH1 and Pvu2 digestion, as well as pGEX1. The resulting plasmid(pGEX1-AC2.4) contains first 672 bp nucleotides of ORF2. pGEX1-AC2.4 was digested with EcoR1 then ligated with the EcoR1 fragment of 1328 bp from pGEX2.2 to give plasmid pGEX-AC2, which contains full length of ORF2.

Selected colonies from each transformant were then induced with isopropylthio-β-D-galactoside (IPTG) and examined for expression of fusion proteins of the expected sizes.

EXAMPLE 3

Production of GST Fusion Proteins

The transformants of pGEX1-AC3, pGEX1-AC2.1 and -2.2, and pGEX1 (as a control) were grown for 5 h in L-Broth medium (LB) containing 50 μg/ml of ampicillin. An aliquot of 0.5 μl of the overnight culture was inoculated into 200 ml of LB plus ampicillin and incubated for 6 hr. IPTG (200 μl of 100 mM stock) was added and the culture was grown overnight. Cells were pelleted at 4000 rpm for 15 min in a bench centrifuge. The pellet was washed in 10 mM Tris (pH 7.5) and spun as before. For each gram of packed cells, 3 μl of lysis buffer (50 mM Tris pH 8.0, 1 mM EDTA, 100 mM NaCl), 4 μl of 100 mM phenylmethylsulfonylfluoride (PMSF) and 80 μl of 10 mg/ml lysozyme were added. The suspension was incubated at room temperature for 30 min then 37° for an additional 30 min. The solution was sonicated for 3 min. and centrifuged at 4000 rpm for 15 min. The pellet (containing most of the fusion proteins) was washed with ice-cold 1M NaCl, 10 mM Tris pH 7.5. The protein pellet was resuspended in 3 ml of 10 mM Tris (pH 7.5), and stored in aliquots at −20°.

EXAMPLE 4

SDS-Polyacrylamide Gel Electrophoresis

Each of the fusion proteins (GST-ORF3, GST-ORF2.1, GST-ORF2.2, GST-ORF2.3, GST-ORF2.4) was thoroughly resuspended in 50 mM Tris (pH 6.8), 2% v/v SDS, 5% v/v 2-mercaptoethanol, 8% v/v glycerol, 0.01% v/v bromophenol blue. In each experiment, unfused GST (prepared as above) was mixed with the fusion proteins before electrophoresis. The protein mixture was heated at 100° for 5 min and loaded on SDS-PAGE gels in a mini-gel apparatus (Bio-Rad, USA) with a separating gel of 10% w/v acrylamide, 0.267% w/v bis-acrylamide, using the discontinuous buffer system of Laemmli (2% w/v SDS, 5% v/v 2-mercaptoethanol, 8% v/v glycerol, 50 mM Tris[pH 6.8], 0.01% w/v bromophenol blue). The gels were electrophorested at 75V for 20 min then 150V until the dye reached the bottom of the gel. The proteins were transferred to nitrocellulose membranes (Hybond-C extra, Amersham) on a Semi-Dry Transfer Cell (Bio-Rad, USA) in transfer buffer (0.15M glycine, 0.025M Tris [pH 8.5], 20% v/v methanol). Biotinylated marker proteins (Bio-Rad) were run in reference lanes.

EXAMPLE 5

Western Blot

The nitrocellulose membranes were blocked with 0.1M Tris (pH7.5), 0.1M NaCl, 0.3% v/v tween-20 (TBST) containing 3% w/v casein and 0.01% w/v sodium azide at room temperature for 1 hr. Test sera were diluted 1:500 in TBST plus 1% w/v casein and preabsorbed with 1% w/v) GST lysate suspension at 37° for 1.5 hr. The diluted sera were incubated at 35° with agitation for 1 hr with the membrane, using the Mini-Proean Multi Screen apparatus (Bio-Rad, USA). The membranes were washed three times for 5 min in TB ST, incubated with horseradish peroxidase (HRPO)-conjugated rabbit anti-human IgG (diluted 1:5000; DAKO Co. Denmark) at 35° for 1 hr, then washed as before. Biotinylated markers were detected using HRPO-conjugated streptavidin (diluted 1:10,000; Amersham). Enzyme complexes were detected by enhanced chemiluminescence (ECL; Amersham). The membranes were soaked in ECL reagents for 1 min, then placed between acetate sheets and exposed to Hyperfilm ECL (Amersham, USA) for 30 sec to 2 min at room temperature.

EXAMPLE 6

Test Sera for Western Blot

Human Acute Hepatitis Sera

Sera from other viral hepatitis cases in Australia were used as negative controls: 10 acute hepatitis A (positive for anti-HAV IgM, Abbot Diagnostics), 18 acute hepatitis B (positive for anti-HBc IgM, Abbot Diagnostics) and 58 hepatitis C (positive in second generation HCV EIA, Abbot Diagnostics). Sixty-six sera were collected from acute phase patients in Xinjiang, China during the Hepatitis E epidemic of 1988.

Serial Sera from Infected Monkeys

Serum specimens were collected approximately twice weekly from 7 rhesus monkeys (M27, M31, M32, M33, M34, M35, M36) experimentally infected with HEV. Samples were stored at −20°.

EXAMPLE 7

Expression of HEV-GST Fusion Proteins

Clones of putative HEV structural proteins were constructed in the highly efficient pGEX expression system, giving rise to proteins fused with GST (normal molecular mass of 26 kDA). The clones studied represent the complete sequence of ORF3 (GST-ORF3), and partially overlapping sequences within ORF2 (GST-ORF2.1, GST-ORF2.2, GST-ORF2.3, GEST-ORF2.4) as shown in FIGS. 5 and 6. After induction with IPTG, bacterial lysates were found to contain unique proteins of about 37, 39.5, 49, 56, 86 and 97 kDa, consistent with the predicted molecular masses of these translated sequences. It should be noted that pGEX1-AC2, pGEX1-AC2.2 and pGEX1-AC2.1 encode proteins having common C-termini (representing the extreme C-terminus of ORF2). pGEX1-AC2.1 encodes 273 amino acids, that is the most C-terminal one-third of ORF2, while pGEX1-AC2.2 has a N-terminal extension of 294 amino acids, and pGEX1-AC2 has a further extension of 93 amino acids and therefore represents 660 amino acids or the full-length ORF2. It should be further noted that pGEX1-AC2, pGEX1-AC2.3 and pGEX1-AC2.4 encode proteins having common N-termini (representing the extreme N-terminus of ORF2). pGEX1-AC2.3 encodes 1509 amino acids, while pGEX1-AC2.4 has a C-terminal extension of 110 amino acids and pGEX1-AC2 has a further extension of 400 amino acids or the full-length ORF2, as above.

EXAMPLE 8

Detection of Anti-HEV by Western Blot

To select conditions for a sensitive diagnostic assay and to examine the dynamics of antibody responses to each fusion protein, western blots were conducted to detect anti-HEV IgG in sera from acute-phase hepatitis patients and from experimentally infected monkeys.

Detection of anti-HEV in human acute hepatitis sera

Sera from well-documented cases of acute hepatitis A, B, C and E were assayed by western blot (FIG. 6, Table 1). The results show that none of 10 Hepatitis A and 18 Hepatitis B sera contained IgG against GST-ORF3 or GST-ORF2.1, but 3 of 58 hepatitis C were weakly reactive to GST-ORF2.1 and one of these was also reactive to GST-ORF3. Sixty-one of 66 (92%) acute HEV sera from Xinjiang contained anti-HEV IgG that bound specifically to the GST-ORF2.1 band but not to the negative control (GST). Of these, 55 were also positive for IgG to GST-ORF3, and one serum was reactive with GST-ORF3 but not with GST-ORF2.1. Nine of nineteen sera collected between 3 and 9 months after suspected HEV were reactive against GST-ORF2.1, but only 3 of these were active with GST-ORF3. When tested using a commercial EIA based on ORF3 of the Burmese and Mexican strains, only one of the convalescent sera was reactive and this serum was reactive against both GST-ORF2.1 and GST-ORF3.

Both fusion proteins were, therefore, immunoreactive by Western blot and resulted in a high detection rate of anti-HEV IgG in epidemic cases of HEV in China, with a high level of specificity indicated by the low reactive rate in other forms of viral hepatitis. Some HEV samples strongly positive for antibody to GST-ORF2.1 or 3 were also reactive with degradation products of the respective fusion proteins (indicated with closed and open circles respectively in FIG. 6 and subsequent figures), but no sera showed reactivity with the control GST protein band.

Detection of Anti-HEV in Serial Sera from Rhesus Monkeys

Rhesus monkeys were inoculated intravenously with a Chinese strain of HEV, and displayed an increase in ALT at 7–26 days indicating acute hepatitis. Serial blood samples were tested for anti-HEV IgG by Western blot. In one monkey (M27), antibodies to both GST-ORF2.1 and GST-ORF3 were detected at day 16, with anti-GST-ORF2.1 continuing to increase throughout the study period whereas anti-GST-ORF3 reached a peak at 71 days and then declined. Degradation products of both fusion proteins were sometimes detected in Western blots, as indicated in subsequent figures.

All 7 monkeys seroconverted since antibody to GST-ORF2.1 was detected at day 14–21, immediately after ALT elevation. Antibody to GST-ORF3 was first detected at the same time or 7 days after first detection of GST-ORF2.1 in four monkeys, but was weakly detectable in only one serum sample from each of 2 monkeys and in no samples from the remaining monkey. Antibody to GST-ORF2.1, therefore, appears to be a more consistent marker of infection in macaques, as was also observed with samples from man (Table 1).

Two monkeys were rechallenged at days 53, 107 and 316, and a third monkey at days 107 and 316 after initial infection. All monkeys have shown biochemical evidence of hepatitis after primary inoculation and less severe hepatitis after the first rechallenge. Only one (M32) of two monkeys appeared to be infected after the second rechallenge, suggesting the acquisition of partial protective immunity after each infection. Coincident with this partial immunity, we detected antibody to GST-ORF2.1 in each monkey remaining at high levels throughout the study and sometimes being boosted after rechallenge. The boosted reactivity may result from limited viral replication or at least partly from viral antigen present in the inocula. It should be noted, however, that in both M31 and M32 no further increase in reactivity was detected following a third rechallenge, which suggests that the increased reactivity observed previously was due to virus replication.

Antibody to GST-ORF3 was detected at high levels in M31 and M32 between days 17 and approximately 60, but waned thereafter. Interestingly, antibody to GST-ORF3 was boosted after the second rechallenge in monkey 32, and in monkey 33 the only sample positive for this antibody was after rechallenge. The reactivity with GST-ORF3 closely reflects that observed using a commercial HEV EIA based on ORF3 synthetic proteins, in which the day 151 sample was also the only reactive sample from M33.

Comparison of GST-ORF2.1 and 2.2

The fusion protein GST-ORF2.1 contains only the carboxy-terminal one-third of the coding sequences from HEV ORF2. In order to examine whether additional sequences from ORF2 would show greater reactivity, sera from monkeys M31, M32 and M33 were reacted with GST-ORF2.1 and GST-ORF2.2, having an N-terminal extension of 294 amino acids. In the acute phase of infection, the extended protein was indeed more strongly reactive, although no samples were positive only for this protein. However, interestingly, the peak reactivity of the extended protein was in fact much lower than that of GST-ORF2.1 in each of the animals. In addition, the antibody was found to decline with time and was only weakly boosted after each rechallenge.

These two proteins were also used to screen some of the sera from patients with acute hepatitis A, B or E as described above, with no difference observed in the proportion of reactive sera, although in most cases the signal for GST-ORF2.2 was stronger than that for GST-ORF2.1, as also seen during the acute phase in monkeys (FIG. 7).

GST fusion proteins GST-ORF2.1, GST-ORF2.2 and GST-ORF2 are partially overlapping with common carboxy termini (FIG. 5, FIG. 6). As shown in FIGS. 3 and 7–10, the shortest of these, GST-ORF2.1, is the most reactive with convalescent hepatitis E sera and therefore is the best protein for expression of the epitopes which are involved in protection from reinfection.

GST fusion proteins GST-ORF2, GST-ORF2.3 and GST-ORF2.4 are partially overlapping with common amino term (FIG. 5). As shown in FIG. 10, the reactivity in sera from experimentally infected macaques against the full-length GST-ORF2 closely approximates that seen with the shorter GST-ORF2.3 and GST-ORF2.4 proteins: that is, they are most reactive with acute phase sera and poorly reactive with convalescent phase sera. The reactivity of full-length GST-ORF2 therefore lies within the region b5147 to 5477 in ORF2 according to Tam, and no reactivity is seen against the sequences b6326 to 7145 which overlap with GST-ORF2.1. The sequences b5147 to 5477 as in GST-ORF2.3 or GST-ORF2.4 are therefore suitable for the detection of acute phase antibodies to HEV, and on the basis of the greater reactivity in macaque M33 compared to that against GST-ORF3, we claim that these proteins will enhance the detection of acute hepatitis E virus infection.

Taken together with the lower reactivity of GST-ORF2.2 and GST-ORF2 compared with GST-ORF2.1 (FIG. 7, FIG. 8), this again suggests that the inclusion of amino terminal sequences of ORF2 inhibits the reactivity of carboxy terminal sequences which may be included in the same protein. It would be expected that they might also reduce the immunogenicity of similar proteins, and we therefore claim that proteins containing sequens between b5147 and 6325 are suitable for diagnostic reagents but not for vaccines unless they can be demonstrated not to interfere with the reactivity of the sequences 6326 to 7145.

It is further claimed that antibodies to GST-ORF3 and/or GST-ORF2.3 and/or GST-ORF2.4 could be used to detect clinical or subclinical infection with HEV in vaccine recipients who have antibodies to GST-ORF2.1 as a result of active or passive immunisation.

EXAMPLE 9

Recent infection can be diagnosed on the basis of antibody to ORF3 and/or increasing titre of antibody to C-terminus ORF2 and/or antibody to the N-terminal part of ORF2, while past infection of HEV can be diagnosed by the presence of antibody to ORF2 with or without antibody to ORF3. Antibody to ORF3 is expected to be present only in a proportion of individuals infected with the virus, and not in individuals who are exposed to viral antigen in the form of an inactivated or live, attenuated vaccine. This is also likely to be true for antibodies to ORF1.

EXAMPLE 10

Development of Vaccines Against HEV

Conventional approaches to recombinant vaccines generally rely on using either synthetic peptides which are small enough to be chemically synthesised, or recombinant or fusion proteins representing as large a portion of the antigen of interest as possible. Consequently, most work on HEV has previously focussed on full-length open reading frame (ORF) 2. However, a key feature of the present invention is the disparity between the length of recombinant HEV proteins and their reactivity. Recombinant protein, GST-ORF2.1, representing only the C-terminal ⅓rd of ORF2, is in fact far more reactive with convalescent sera than is a full length GST-ORF2 protein. Furthermore, the reactivity of the full length protein is most likely attributable to the N-terminal sequences, as its reactivity with convalescent sera almost exactly mirrors that of such N-terminal proteins (FIG. 8). Full-length ORF2, therefore, does not efficiently present the epitopes found in GST-ORF2.1, which are likely to be important for protective humoral immunity.

EXAMPLE 11

The fragment designated ORF2.1, representing the C-terminal 267 amino acids of the 660 in ORF2 expressed in *E. coli*, demonstrated long-lasting IgG reactivity associated with both acute and convalescent phases of infection (Li, et al. (1994)). The ORF2.1 fragment formed antigenic epitopes which were not present in other recombinant HEV antigens expressed in *E. coli* and ORF2.1 had optimal reactivity with convalescent serum from experimentally infected macaques (Li, et al. (1997a); Li, et al. (1994)).

We examined the reactivity of human acute (A) and human convalescent sera (B) against a panel of mutants representing C-terminal fragments of ORF2, including ORF2.1, and the recombinant proteins SG3, C2 and 406.3-2 known from prior art. As shown in FIG. 9A, acute-phase sera from a patient infected in Asia reacted 1equally with all constructs, even the smallest (406.3-2+), but in FIG. 9B it is shown that a convalescent patient serum reacted only with the 2.1 fragment. Addition or deletion of as few as 20 HEV—specific amino acids to the N-terminus of 2.1 destroyed this reactivity, seen in 2.1+1 and 2.1−1, respectively. SG3+ and C2, which were larger than 2.1+1, also lost this convalescent reactivity.

All of the primary amino acid sequence present in ORF2.1 was present in each of the larger recombinant proteins, and yet these larger recombinant proteins did not form the epitope which was reactive with convalescent sera. The major ORF2.1 epitope reactive with convalescent antibody was therefore a conformational epitope, the correct folding of which was perturbed by the inclusion of additional HEV-specific sequences at the N-terminus of ORF2.1 or the N-terminal junction of ORF2.1 and a fusion protein partner of choice (in this case, GST), for expression in prokaryotic cells.

A similar pattern of "conformational" reactivity was seen in rats immunized with recombinant 2.1 protein (see FIGS. 9C, 9D and 9E). At 2 weeks after the first immunization, rats developed antibody to a wide range of ORF2 fragments, but by 10 weeks (6 weeks after boosting) the ORF2.1 conformational reactivity was dominant, and by 27 weeks reactivity was almost exclusively against ORF2.1. Therefore, although early antibody responses were directed against a broad range of ORF2 epitopes, this specificity rapidly matured to a more narrow, 2.1-specific reactivity. Further, ORF2.1 protein not only detected, but also induced antibody to this conformational epitope.

A similar pattern of reactivity was also seen in patients infected with the highly divergent, Mexico strain of HEV (FIG. 10). In this patient, 7 months after onset of disease, ORF2.1 was by far the most reactive protein, with 406.3-2, SG3 and C2 having negligible reactivity. The ORF2.1 conformational epitope was therefore highly conserved between divergent strains of HEV, allowing this single antigen to be used for diagnosis or immunization against all strains of HEV. In contrast, current diagnostic assays must include the ORF3 sequence of the Mexico strain in order to detect infections with this strain, and the isolation of further divergent strains in the U.S.A. and Africa highlights the importance of this conserved epitope.

Moreover, experimental immunization of macaques with a TrpE-C2 fusion protein provided partial protection against homologous, but not heterologous challenger with virulent HEV (Purdy, et al. (1993)). Our results showed that convalescent antibody included reactivity against the ORF2.1 conformational epitope which was not present in C2 (FIG. 9). The results also demonstrated that immunization with ORF2.1 protein induced antibody to this conformational epitope which suggested that ORF2.1 provides protection against both homologous and heterologous strains of HEV.

EXAMPLE 12

FIGS. 13 and 14 show four independent monoclonal antibodies derived from hybridoma cell lines established using mice immunized with the ORF2.1 protein. HEV-specific antibody production was detected by ELISA using ORF2.1 as the antigen. In FIG. 13, western immunoblotting of identical panels of ORF2 recombinant proteins to those shown in FIGS. 9 and 10 revealed that 2 of the 4 monoclonal antibodies reacted with linear epitopes which were present in all constructs containing sequences N-terminal to the end of ORF2.1-2 (clone 1E6) or ORF2.1-1 (clone 1C7), and therefore represented linear epitopes in the Sequences 414–434 and 394–414, respectively. In contrast, the other two monoclonal antibodies clearly reacted with the ORF2.1-specific, conformational epitope, mimicking convalescent patient antibody. FIG. 12 shows that the conformational epitope, which is unique to ORF2.1 among recombinant proteins expressed in *E. coli,* was also present in full-length ORF2 when this protein (660 amino acids) was expressed in mammalian cells, in this case using the Semliki Forest Virus replicon (Torresi, et al. (1997)). The presence of this epitope in full-length ORF2 protein expressed in mammalian cells demonstrate that this is a neutral epitope of ORF2 which is masked when most recombinant proteins (other than ORF2.1) are expressed in E. coli.

EXAMPLE 13

ORF2.3 and ORF2.4 antigens demonstrated high levels of reactivity with acute-phase HEV sera, but this reactivity rapidly declined over a period of months, in a similar way to reactivity against ORF3 (Li, et al. (1997a)). Antibody reactivity to ORF2.3 and/or ORF2.4 was therefore indicative of acute HEV infection, and the detection of IgM reactivity against these antigens provided further evidence of acute infection.

The epitopes within the ORF2.3 and ORF2.4 fragments were the only part of the HEV-specific antigenic repertoire which were efficiently exposed when the full-length protein was expressed in E. coli, with antibody to the full-length protein exactly mirroring that against the smaller, N-terminal fragments (Li, et al. (1997a)).

Those skilled in the art will appreciate that the invention described herein is susceptible to variations and modifications other than those specifically described. It is to be understood that the invention includes all such variations and modifications. The invention also includes all of the steps, features, compositions and compounds referred to our indicated in this specification, individually or collectively, and any and all combinations of any two or more of said steps or features.

TABLE 1

Detection of anti-HEV IgG by Western Blotting

| Infection | Number | Number positive (%) GST-ORF2.1GST-ORF3 | | Total (%)[a] |
|---|---|---|---|---|
| Hepatitis A | 10 | 0 | 0 | 0 |
| Hepatitis B | 18 | 0 | 0 | 0 |
| Hepatitis C | 58 | 3(5) | 1(2) | 3(5) |
| Hepatitis E (acute)[b] | 66 | 61(92) | 56(85) | 62(94) |
| Hepatitis E (convalescent)[c] | 19 | 9(47) | 3(16) | 9(47) |

[a]Positive for GST-ORF2.1 and/or GST-ORF3.
[b]Less than three months after onset of disease
[c]Three to nine months after onset of disease

BIBLIOGRAPHY

ANDIAPARIDZE, A. G., BALAYAN, M. S. SAVINOV, A. P., BRAGINEKY, D. M., POLESCHIJK, V. F. and ZAMYATINA, N. A. (1986). Fecal-Oral transmitted non-A, non-B hepatitis induced in monkeys. Vopr. Virusol. 1, 73–80.

ARANKALLE, V. A., TICEHURST, L., SREENIVASAN, M. A. et al. (1988). Aetiological association of a virus-like particle with enterically transmitted non-A, non-B hepatitis. Lancet 1, 550–554.

AYE, T. T. et al (1992). Sequence comparison of the capsid region of hepatitis E viruses isolated from Myanmar and China Microbial-Immunol 36(6) 615–21.

BALAYAN, M. S., ANDJAPARIDZE, A. G., SAVINBKAYA, S. S., et al. (1983). Evidence for a virus in non-A, non-B hepatitis transmitted via the fecal-oral route. Intervirology 20, 23–31.

BRADLEY, D. W. (1990a). Hepatitis non-A, non-B viruses become identified as hepatitis C and E viruses. Prog. Med. Virol. 37, 101–135.

BRADLEY, D. W. (1990b). Enterically transmitted non-A, non-B hepatitis. Br Med. Bull. 46, 442–461.

BRADLEY, D. W., and MAYNARD, I. E. (1986). Etiology and natural history of post-transfusion and enterically-transmitted non-A, non-B hepatitis, Sem. Liver Dis. 6, 56–66.

BRADLEY, D. W., KRAWCZYNSKI, K., COOK, E. H., Jr, et al. (1987). Enterically transmitted non-A, non-B hepatitis: serial passage of disease in cynomolgus macaques and tamarins and recovery of disease associated 27- to 34-nm viruslike particles. Proc. Nati. Acad. Sci. USA 84, 6277–6281.

BRADLEY, D. W., KRAWCZYNSKI, K., COOK, E. H., Jr, et al. (1988a). Enterically transmitted non-A, non-B hepatitis: Etiology of disease and laboratory studies in non human primates in "Viral Hepatitis and Live Disease" (A. J. Zuckerman, Ed.). pp 138–147. A. R. Liss, New York.

CAO, X, MA, X, LIU Y, et al. Epidemiological and etiological studies on enterically transmitted non-A, non-B hepatitis in the south part of Xinjiang, China. Chinese Journal of Experimental and Clinical Virology, 1989, 3(2): 1–9.

CHOO, G. L., KUO, G., WEINER, A. J., OVERBY, L. R., BRADLEY, D. W., and HOUGHTON, M., (1989). Isolation of cDNA clone derived from a blood-borne non-A, non-B viral hepatitis genome. Science 244, 359–362.

FEINSTONE, S. M., KAPIKIAN, A. Z., PURCELL, R. H., ALTER, H. J., and HOLLAND, P. V. (1975). Transfusion associated hepatitis not due to viral hepatitis type A or B. N. Engl. J. Med. 292, 767–770.

KHUROO, M. S. (1990). Study of an epidemic of non-A, non-B hepatitis: Possibility of another human hepatitis virus distent from post-transfusion non-A, non-B type. Am. J. Med. 68, 818–824.

KRAWCZYNSKI, K., and BRADLEY, G. W., (1989). Enterically transmitted non-A, non-B hepatitis: Identification of cirus associated antigen in experimentally infected cynomolgus macaques. J. Infect, Dis. 159, 1042–1049.

KUBO, Y., TAKEUCHI, K., BOONMAR, S., et al, (1989). A cDNA fragment of hepatitis C virus isolated from an implicated donor of post-transfusion non-A, non-B hepatitis in Japan. Nucleic Acids Res. 17,10,367–10,372.

KUO, G., CHOO, G. L., ALTER, H. I., et al, (1988). An essay for circulating antibodies to a major etiologic virus of human non-A, non-B hepatitis. Science 244, 362–364.

MAENO, M., KAMINAKA, K., SUGIMOTO, H., et al, (1990). A cDNA clone closely associated with non-A, non-B hepatitis. Nucleic Acids Res. 18, 2685–2689.

MANIATIS et al (1982). Molecular Cloning: A Laboratory Manual, Cold Spring Harbor Laboratories, Cold Spring Harbor, N.Y., USA PRINCE, A. M., BROTMAN, B., and GRADY, G. F., (1974). Long-incubation post-transfusion hepatitis without serological evidence of exposure to hepatitis B virus. Lencer 2, 241–246.

PURCELL, R. H., and TICEHURST, J. R., (1988). Enterically transmitted non-A, non-B hepatitis; epidemiology and clinical characteristics in "Viral Hepatitis and Liver Disease" (A. J. Zuckerman, Ed). pp 131–137, A. R. Liss, New York REYES., G. R., and BAROUDY., G. M., (1991). Molecular biology of non-A, non-B hepatitis agents; The hepatitis C and hepatitis E viruses in "Advances in Virus Research" (K. Maramorosch, F. A. Murphy, and A. J. Shatkin, Eds.). Vol 40, pp 55–101. Academic Press, Orlando.

REYES, G. R., PURDY, M. A., KIM, F. P., et al. (1990), Isolation of a cDNA from the virus responsible for enterically transmitted non-A, non-B hepatitis. *Science* 247, 1335–1339.

TABOR, E. (1985). The three viruses of non-A, non-B hepatitis. *Lancet* 1, 743–745.

TAM, A. W., SMITH, M. M., GUERRA, M. E., HUANG, C-C., BRADLEY, D. W., FRY, K. E., REYES, G. R. (1991). Hepatitis E virus (HEV): Molecular cloning and Sequencing of the Full length viral genome. *Virology* 185, 120–131.

WILSON, K. M., GERAMETTEO, M., RYLATT, D. B., BUNDESEN, P. D., McPHEE, D. A., KEMP, B. E., (1991) Rapid whole blood assay for HIV-1 seropositivity using an Fab-peptide conjugate, *J. Immunol. Methods* 138, 111–119.

WONG, D. C., PURCELL, R. H., SREENIVABAN, M. A., PRABAO, S. R., and PAVRI, K. M. (1980). Epidemic and andemic hepatitis in India: evidence for a non-A, non-B hepatitis virus aetiology, *Lancet* 2, 876–879.

What is claimed is:

1. A method for detecting Hepatitis E virus (HEV) acute phase antibodies in a biological sample comprising contacting said biological sample with a polypeptide for a time and under conditions sufficient to permit a complex to form with HEV antibodies if present in said biological sample and detecting the complex, wherein said polypeptide comprises an ORF2 polypeptide consisting of amino acids 394–660 of HEV.

2. The method according to claim 1 wherein said biological sample is whole blood, plasma, serum or saliva.

3. A method for detecting Hepatitis E Virus (HEV) convalescent phase antibodies in a biological sample, comprising contacting said biological sample with a polypeptide for a time and under conditions sufficient for a complex to form with HEV antibodies, if present in said biological sample, and detecting said complex, wherein said polypeptide is produced by expression of a nucleic acid molecule comprising a 3' end portion of SEQ ID:NO: 1.

4. The method according to claim 3 wherein said biological sample is whole blood, plasma, serum or saliva.

5. The method according to claims 1 or 3 wherein said polypeptide further comprises a non-HEV polypeptide.

6. The method according to claim 5 wherein the non-HEV polypeptide is GST or a derivative thereof.

7. A method for detecting Hepatitis E virus (HEV) acute phase antibodies in a biological sample comprising contacting said biological sample with a polypeptide for a time and under conditions sufficient to permit a complex to form with HEV antibodies if present in said biological sample and detecting the complex, wherein said polypeptide comprises an ORF2 polypeptide of HEV consisting of amino acids as set forth in SEQ ID NO: 18, SEQ ID NO: 22 or SEQ ID NO:24.

8. A method for detecting Hepatitis E virus (HEV) acute phase antibodies in a biological sample comprising contacting said biological sample with a polypeptide for a time and under conditions sufficient to permit a complex to form with HEV antibodies if present in said biological sample and detecting the complex, wherein said polypeptide is produced by expression of a 3' end sequence of SEQ ID NO:1.

9. A method for detecting Hepatitis E virus (HEV) acute phase antibodies in a biological sample comprising contacting said biological sample with a polypeptide for a time and under conditions sufficient to permit a complex to form with HEV antibodies if present in said biological sample and detecting the complex, wherein said polypeptide is produced by expression of nucleotides as set forth in SEQ ID NO:17, SEQ ID NO:21 or SEQ ID NO:23.

10. A method for detecting Hepatitis E Virus (HEV) convalescent phase antibodies in a biological sample, comprising contacting said biological sample with a polypeptide for a time and under conditions sufficient for a complex to form with HEV antibodies, if present in said biological sample, and detecting said complex, wherein said polypeptide is produced by expression of a nucleic acid molecule comprising a 3' end portion of SEQ ID:NO:17.

11. A method for detecting Hepatitis E Virus (HEV) convalescent phase antibodies in a biological sample, comprising contacting said biological sample with a polypeptide for a time and under conditions sufficient for a complex to form with HEV antibodies, if present in said biological sample, and detecting said complex, wherein said polypeptide comprises a sequence of amino acids as set forth in SEQ ID NO: 18.

12. The method according to claims 7, 8, 9, 10 or 11 wherein said biological sample is whole blood, plasma, serum or saliva.

13. The method according to claims 7, 8, 9, 10 or 11 wherein said polypeptide further comprises a non-HEV polypeptide.

14. The method according to claim 13 wherein the non-HEV polypeptide is GST or a derivative thereof.

15. A kit for detecting antibodies to HEV, said kit comprising in compartmental form, a first compartment containing one or more polypeptides comprising an ORF2 polypeptide consisting of amino acids 394 to 660 of HEV, said kit further comprising one or more compartments comprising agents suitable for detecting antibodies.

16. A kit for detecting antibodies to HEV, said kit comprising in compartmental form, a first compartment containing one or more ORF2 polypeptides of HEV consisting of amino acids as set forth in SEQ ID NO:18, SEQ ID NO:22 or SEQ ID NO:24, said kit further comprising one or more compartments comprising agents suitable for detecting antibodies.

17. A kit for detecting antibodies to HEV, said kit comprising in compartmental form a first compartment containing one or more polypeptides produced by expression of a 3' end nucleotide sequence of SEQ ID NO:1.

18. A kit for detecting antibodies to HEV, said kit comprising in compartmental form a first compartment containing one or more polypeptides produced by expression of a sequence of nucleotides as set forth in SEQ ID NO:17, SEQ ID NO:21 or SEQ ID NO:23.

\* \* \* \* \*

UNITED STATES PATENT AND TRADEMARK OFFICE
CERTIFICATE OF CORRECTION

PATENT NO.    : 6,514,690 B1
DATED         : February 4, 2003
INVENTOR(S)   : David A. Anderson et al.

It is certified that error appears in the above-identified patent and that said Letters Patent is hereby corrected as shown below:

<u>Title page,</u>
Item [75], "Stephen Alistair Logarnini" should read -- Stephen Alister Locarnini --

Signed and Sealed this

Eighth Day of July, 2003

JAMES E. ROGAN
*Director of the United States Patent and Trademark Office*